United States Patent [19]

Wissner et al.

[11] Patent Number: 5,215,975

[45] Date of Patent: Jun. 1, 1993

[54] CERTAIN HYDROXY-PHOSPHINYL-OXY-PHENYL METHYL-THIAZOLIUM HYDROXIDE INNER SALTS AS PAF ANTAGONISTS

[75] Inventors: Allan Wissner, Ardsley, N.Y.; Robert E. Schaub, Upper Saddle River, N.J.; Phaik-Eng Sum, New City, N.Y.

[73] Assignee: American Cyanamid Company, Stamford, Conn.

[21] Appl. No.: 763,716

[22] Filed: Sep. 23, 1991

Related U.S. Application Data

[63] Continuation of Ser. No. 316,721, Mar. 3, 1989, abandoned, which is a continuation-in-part of Ser. No. 177,299, Apr. 4, 1988, abandoned.

[51] Int. Cl.$^5$ ................ C07F 9/6539; A61K 31/67; A61K 31/675
[52] U.S. Cl. ................ 514/92; 544/232; 544/242; 544/337; 546/22; 546/23; 548/112
[58] Field of Search ................ 548/112; 514/92

[56] References Cited

U.S. PATENT DOCUMENTS

| 4,697,031 | 9/1987 | Wissner et al. | 558/169 |
| 4,699,990 | 10/1987 | Wissner et al. | 558/169 |
| 4,900,731 | 2/1990 | Wissner et al. | 514/77 |
| 4,983,592 | 1/1991 | Wissner et al. | 514/92 |

OTHER PUBLICATIONS

Wissner et al., "Analogues of PAF, Some Modifications of the Alkoxy Chain", p. 34, Journal of Medicinal Chemistry, 1984, vol. 27, No. 9.
Wissner et al., "Analogues of PAF", p. 1653, Journal of Medicinal Chemistry, 1992, vol. 35, No. 9.

Primary Examiner—Alan L. Rotman
Attorney, Agent, or Firm—H. G. Jackson

[57] ABSTRACT

The invention is a compound of R or S enantiomers or racemic mixtures of compounds of the formula:

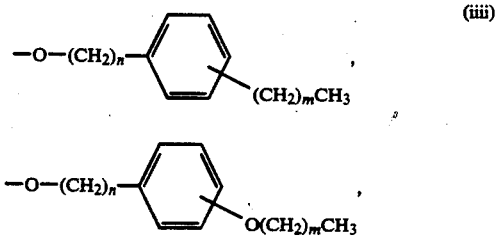

Formula I wherein:
(A) X is
  (i) $C_1$–$C_{24}$
  (ii) $C_1$–$C_{24}$ alkoxy;
  (iii) $C_1$–$C_{24}$ carboamoyloxy;

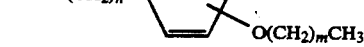

(iiii)

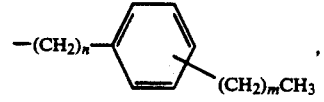

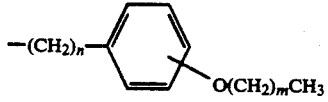

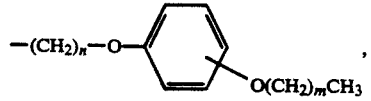

(Abstract continued on next page.)

-continued

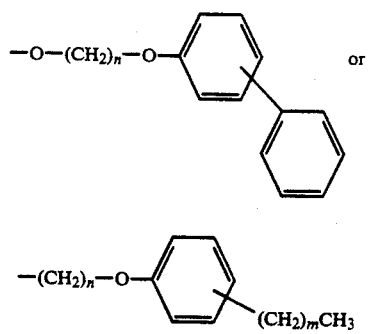

wherein n is an integer from 1 to 25 and m is an integer from 0 to 24 and the sum of n and m is less than or equal to 25;
(v) phenyl;
(vi) mono-or polysubstituted phenyl substituted with $C_1$–$C_{20}$ alkoxy, halogen, trifluoromethyl, phenyl, or benzyloxy;
(vii) phenoxy;
(viii) mono- or polysubstituted phenoxy substituted with $C_1$–$C_{20}$ alkyl, $C_1$–$C_{20}$ alkoxy, halogen, trifluoromethyl, phenyl, or benzyloxy;
(ix) naphthaloxy;
(x) mono- or polysubstituted naphthaloxy substituted with $C_1$–$C_{20}$ alkyl, $C_1$–$C_{20}$ alkoxy or halogen;
(B) i is an integer from 1 to 3 and j is an integer from 1 to 6;

(C) Q is —$OR_2$,

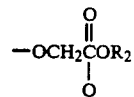

or O—C—$R_2$, wherein $R_2$ is hydrogen, $C_1$–$C_6$ alkyl or $C_1$–$C_6$ alkenyl;
(D) Y is the divalent radical

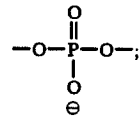

(E) the moiety $R_3$ represents one or more $C_1$–$C_5$ alkyl, $C_1$–$C_5$ alkoxy or halogen substituents of the aromatic ring;
(F) the moiety —$CH_2A$ may be in the ortho, meta or para position wherein A is the
(i)

which are PAF inhibitors.

28 Claims, No Drawings

CERTAIN HYDROXY-PHOSPHINYL-OXY-PHENYL METHYL-THIAZOLIUM HYDROXIDE INNER SALTS AS PAF ANTAGONISTS

This is a continuation of co-pending application Ser. No. 07/316,721, filed on Mar. 3, 1989, now abandoned which is a continuation-in-part of Ser. No. 177,299 filed on Apr. 4, 1988, now abandoned.

BACKGROUND OF THE INVENTION

Platelet Activating Factor (PAF), 1-0-hexadecyl-/octadecyl-2-acetyl-sn-glyceryl-3-phosphorylcholine, is an ether lipid produced by a variety of different cell types. Recent studies [Snyder, F., Ann. Rep. Med. Chem., 17, 243 (1982); Pinckard, R. N., et. al., J. Adv. Inflammation Res., 4, 147 (1982); O'Flaherty, J. T., et. al., Clin. Rev. Allergy, 1, 353 (1983); Vargaftig, B. B., et. al., J. Trends. Pharmacol. Sci., 4, 341 (1983)] have shown PAF to be an important mediator of allergic disease. Included among the physiological processes in which PAF is implicated are aggregation of platelets, inflammation, smooth muscle contraction, pain and edema. PAF is implicated in asthma, respiratory distress syndrome, lung edema and other inflammatory and cardiovascular diseases.

The compounds of the present invention have proven to be specific inhibitors of the biological effects of PAF and are consequently useful for the treatment of asthma, anaphylactic, and septic shock, psoriasis, bowel necrosis, adult respiratory distress syndrome, transplant rejection, thrombosis, stroke, cardiac anaphylaxis and cancer.

BRIEF SUMMARY OF THE INVENTION

The compounds of the present invention include the individual R and S enantiomers and racemic mixtures represented by the formula I.

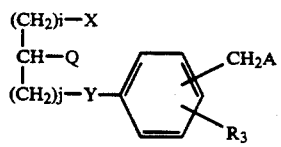

Formula I wherein:

(A) X is selected from the group consisting of
  (i) $C_1$–$C_{24}$ alkyl;
  (ii) $C_1$–$C_{24}$ alkoxy;
  (iii) $C_1$–$C_{24}$ carboamoyloxy;

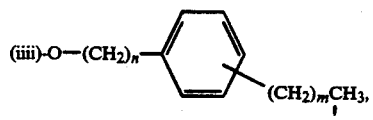

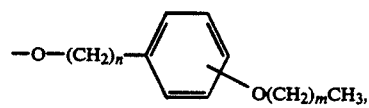

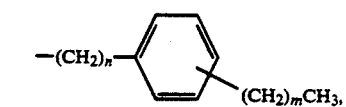

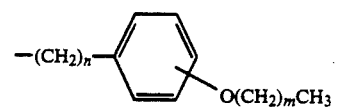

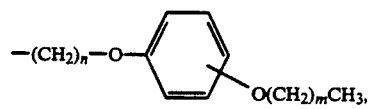

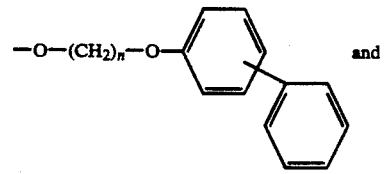

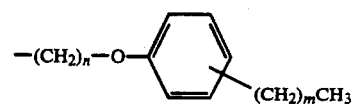

wherein n is an integer from 1 to 25 and m is an integer from 0 to 24 and the sum of n and m is less than or equal to 25;

(v) phenyl;

(vi) mono- or polysubstituted phenyl wherein the substituents are selected from the group consisting of $C_1$–$C_{20}$ alkyl, $C_1$–$C_{20}$ alkoxy, halogen, trifluoromethyl, phenyl, substituted phenyl and benzyloxy;

(vii) phenoxy;

(viii) mono- or polysubstituted phenoxy wherein the substituents are selected form the group consisting of $C_1$–$C_{20}$ alkyl, $C_1$–$C_{20}$ alkoxy, halogen, trifluoromethyl, phenyl, substituted phenyl and benzyloxy;

(ix) naphthaloxy;

(x) mono- or polysubstituted naphthaloxy wherein the substituents are selected from the group consisting of $C_1$–$C_{20}$ alkyl, $C_1$–$C_{20}$ alkoxy and halogen;

(xi) $-O-(CH_2)_r-O-((CH_2)_pO)_t-(CH_2)_a-W$ wherein W is selected from the group consisting of methyl and phenyl optionally substituted with $C_1$–$C_3$ alkyl, $C_1$–$C_3$ alkoxy and phenyl, r, p, t and a are integers such that the expression $r+(p+1)t+a$ is also an integer and has a value of 3 to 20; r is greater than or equal to 2; p is greater than or equal to 2; t is greater than or equal to zero; and a is greater than or equal to zero;

(B) i is an integer from 1 to 3 and j is an integer from 1 to 6;

(C) Q is selected from the group consisting of $-OR_2$,

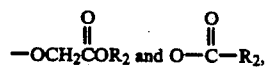

wherein $R_2$ is hydrogen, $C_1$–$C_6$ alkyl or $C_1$–$C_6$ alkenyl;

(D) Y is a divalent radical selected from the group consisting of

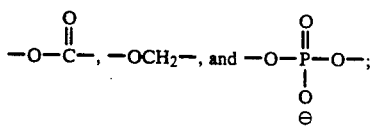

(E) the moiety R$_3$ represents one or more substituents of the aromatic ring selected from the group consisting of C$_1$–C$_5$ alkyl, C$_1$–C$_5$ alkoxy and halogen;

(F) the moiety —CH$_2$A represents a substituent of the aromatic ring which may be in the ortho, meta or para position wherein A is selected from the group consisting of:
  (i) a 5–7 member aromatic heterocyclic ring containing at least one nitrogen atom and one or more nitrogen or sulfur atoms;

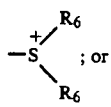

A preferred embodiment is compounds of formula I, above, wherein A is:

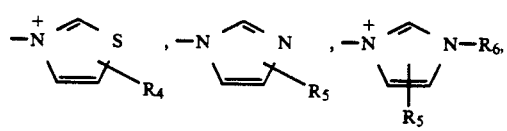

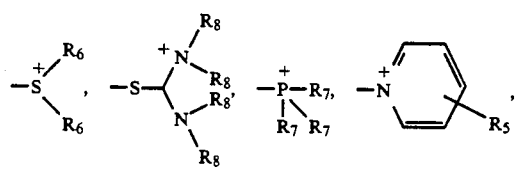

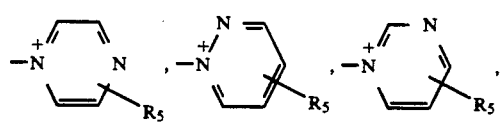

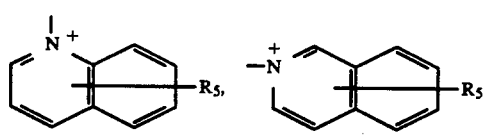

wherein
(a) R$_4$ represents one or more substituents of the heterocyclic ring which may occupy any non-hetero atom position and is selected from the group consisting of:
  (i) C$_1$–C$_5$ alkyl;
  (ii) C$_1$–C$_5$ alkoxy;
  (iii) halogen;
  (iv) —CH$_2$CH$_2$OH; and
  (v) hydrogen
(b) R$_5$ represents one or more substituents of the heterocyclic ring which may occupy any non-heteroatom position and is selected from the group consisting of
  (i) C$_1$–C$_5$ alkyl;
  (ii) C$_1$–C$_5$ alkoxy;
  (iii) halogen; and
  (iv) hydrogen;
(c) R$_6$ is C$_1$–C$_5$ alkyl; and
(d) R$_7$ is C$_1$–C$_5$ alkyl, phenyl or substituted phenyl.
(e) R$_8$ is C$_1$–C$_5$ alkyl or hydrogen.

Such compounds are useful for the treatment of asthma, anaphylactic shock, septic shock, psoriasis, adult respiratory distress syndrome, transplant rejection, thrombosis, stroke, cardiac anaphylaxis, bowel necrosis and cancer.

DETAILED DESCRIPTION OF THE INVENTION

The preparation of compounds of this invention encompassed by formulas IA–C is described hereinbelow in Flowsheet A wherein X, i, j, R$_3$, R$_6$ and A are as described hereinabove; Q$^1$ is selected from the group

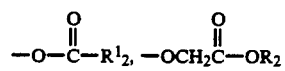

and —OR$^1$$_2$, wherein R$^1$$_2$ is C$_1$–C$_6$ alkyl or C$_1$–C$_6$ alkenyl; the moieties —CH$_2$—J and —CH$_2$—A are substituents of the aromatic ring coming off the meta and para positions, wherein A$^1$ is a nitrogen containing heterocycle, a sulfide, thiourea, or a phosphine selected from the group:

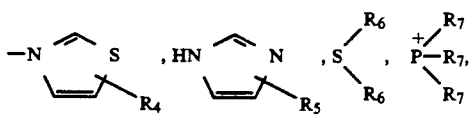

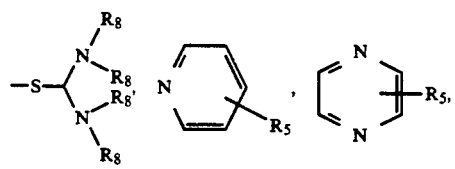

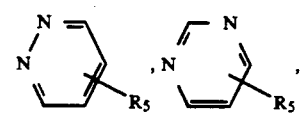

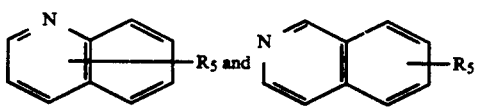

wherein R$_4$ represents one or more substituents of the heterocyclic ring which may occupy any non-hetero atom position and is selected from the group consisting of C$_1$–C$_5$ alkyl, C$_1$–C$_5$ alkoxy, hydrogen, halogen and —CH$_2$CH$_2$OH; R$_5$ represents one or more substituents of the heterocyclic ring which may occupy any non-hetero atom position and is selected from the group consisting of C$_1$–C$_5$ alkyl, C$_1$–C$_5$ alkoxy, hydrogen, and halogen; R$_6$ is C$_1$ to C$_5$ alkyl; R$_7$ is C$_1$–C$_5$ alkyl, phenyl and substituted phenyl R$_8$ is hydrogen or C$_1$–C$_6$ alkyl and J is a leaving group such as a chlorine, bromine or iodine atom.

According to the sequence of reactions outlined in Flowchart A, the alcohol 2 is treated with an equivalent of the phosphorus reagent 3 in the presence of a base such as triethylamine in an inert solvent such as carbon tetrachloride to give, after hydrolysis of the resulting intermediate in a buffered solvent system such as tetrahydrofuran-water-sodium acetate, the phosphate 4. The reaction of 4 with a large excess of a nitrogen containing heterocycle, a sulfide, thiourea, or a phosphine in an inert solvent such as toluene at 50°-150° C. gives the compounds of this invention represented by formula IA. These compounds are obtained as internal salts except when A is an imidazole moiety.

In those cases where the compounds contain an imidazole ring (Formula IB), the imidazole moiety can be further alkylated with an excess of alkyl halide by heating in an inert solvent such as toluene to give the internal salts IC.

inert solvent such as toluene at 50°-150° C. gives the compounds of this invention represented by formula ID. These compounds are obtained as internal salts except when A is an imidazole moiety. In those cases where the compounds contain an imidazole ring (formula IE), the imidazole moiety can be further alkylated with an excess of alkyl halide by heating in an inert solvent such as toluene to give the internal salts IF.

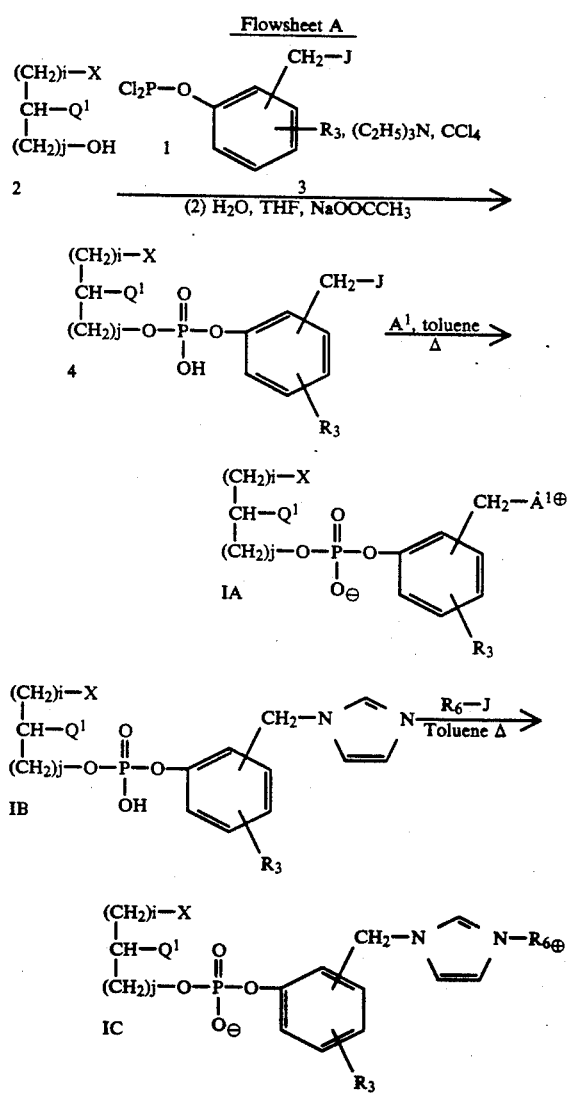

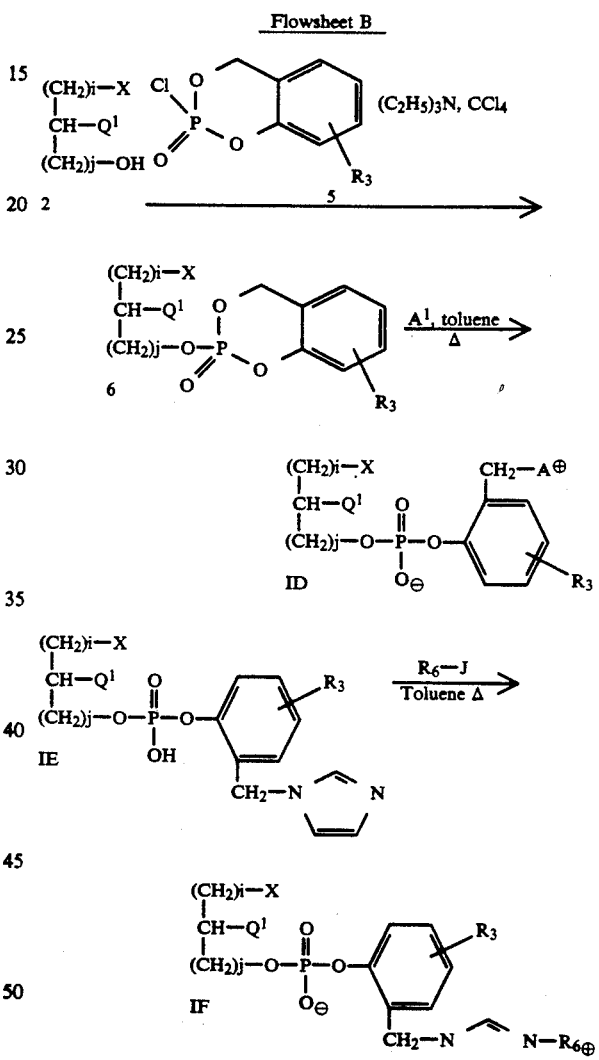

The preparation of compounds of this invention encompassed by formulas ID-IF is described hereinbelow in Flowchart B wherein X, i, j, $R_3$, $R_6$, A, $A^1$, $Q^1$ and J are as defined hereinabove.

According to the sequence of reactions outlined in Flowchart B, the alcohol 2 is treated with an equivalent of the phosphorus reagent 5 in the presence of a base such as triethylamine in an inert solvent such as carbon tetrachloride to give the cyclic phosphate 6. The reaction of 6 with a large excess of a nitrogen containing heterocycle, a sulfide, thiourea or a phosphine in an The phosphorous reagents represented by formulas 7a and 7b needed to prepare some of the compounds of this invention are prepared as described hereinbelow in Flowsheet C and in copending application Ser. No. 679,788, filed Dec. 10, 1984 (Case 29,706) wherein $R_3$ is as defined hereinabove and $J^1$ is chlorine or bromine.

According to the reaction outlined in Flowsheet C, the phenols 8a or 8b are reacted phosphorousoxychloride and at least one equivalent of an amine base such as triethylamine in an inert solvent such as carbon tetrachloride to give the phosphorous reagents 7a and 7b.

Flowchart C

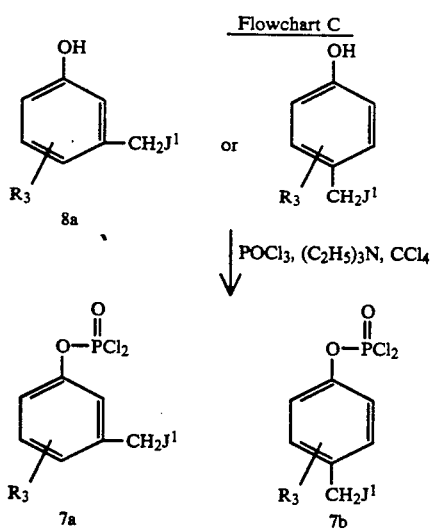

The cyclic phosphorous reagents represented by formula 9 needed to prepare some of the compounds of this invention are prepared as described hereinbelow in flowsheet D wherein R₃ is as defined hereinabove.

According to the reactions outlined in flowsheet D, the hydroxy phenol 10 is treated with an equivalent of phosphorous trichloride in an inert solvent such as ether in the presence of at least two equivalents of pyridine to give compound 11. Oxidation of 11 with a dry stream of oxygen in benzene then furnishes the phosphorous reagent 9.

Flowsheet D

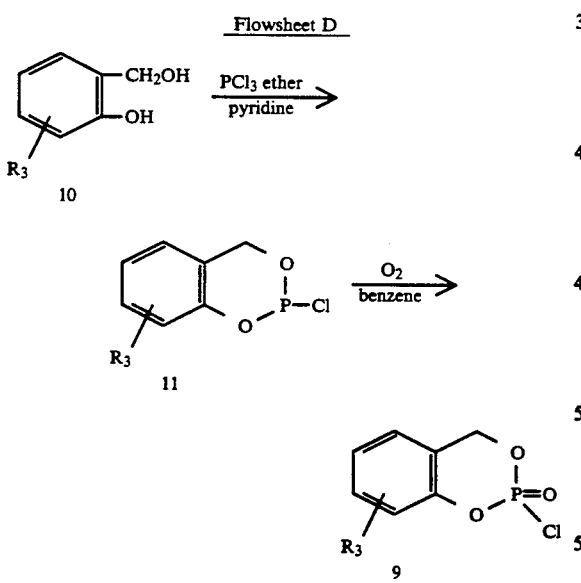

Compounds of this invention represented by formulas 16a-c are prepared as described hereinbelow in flowsheet E, wherein R₃, J′, J, X, Q′, i, j, A′ and A are as defined hereinabove.

According to the reactions outlined in flowchart E the carboxylic acid 13 is converted to the acid chloride 14 by the reaction with oxalyl chloride in dichloromethane in the presence of a catalytic amount of dimethylformamide. The acid chloride 14 is then treated with an equivalent of the alcohol 2 in an inert solvent such as tetrahydrofuran in the presence of at least one equivalent of an amine base such as pyridine to give the ester 15. The reaction of 15 with a large excess of a nitrogen containing heterocycle, a sulfide, thiourea, or a phosphine in an inert solvent such as toluene at 50°–150° C. gives the compounds of this invention represented by formula 16a. These compounds are obtained as salts except when A is an imidazole moiety. In those cases where the compound contains an imidazole ring (formula 16b), the imidazole moiety can be further alkylated with an excess of alkyl halide by heating in an inert solvent such as toluene to give the salts 16c.

Flowsheet E

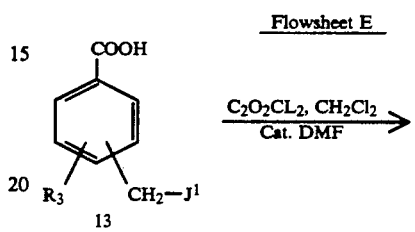

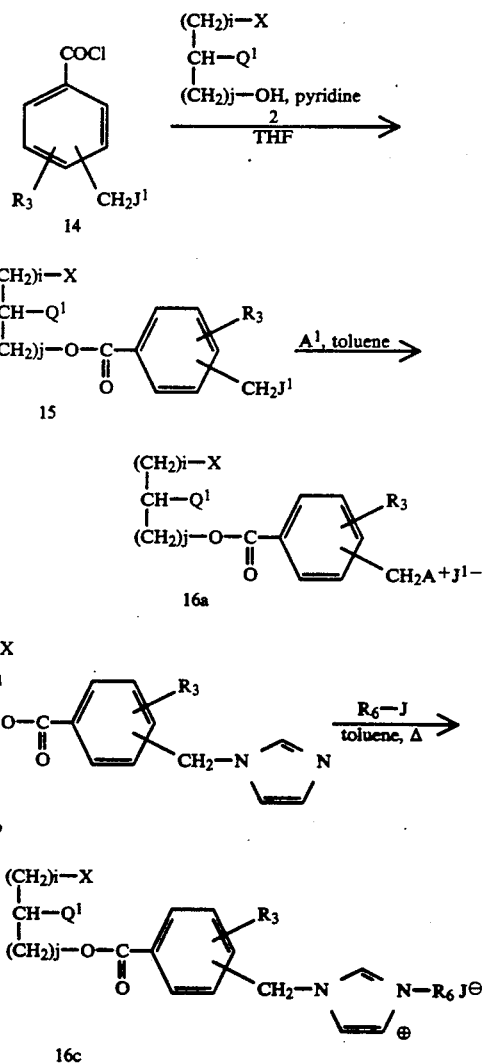

Compounds of this invention represented by formulas 22a-c are prepared as described hereinbelow in flowsheet F wherein R₂, R₃, J′, J, X, i, j, A′ and A are as defined hereinabove and Q″ is OR₂′″, where R₂ ′″ is selected from the group consisting of $C_1-C_6$ alkyl, $C_1-C_6$ alkenyl, or tetrahydropyranyl.

According to the reactions outlined in flowsheet F, the alcohol 17 is converted to the corresponding tosylate using p-toluensulfonyl chloride in pyridine. Addition of 18 to a dimethylformamide solution of the sodium salt of diol 19 gives the monoalkylated product 20 which is separated from the dialkylated product and unreacted 19 by chromatography on silica gel. The reaction of 20 with methane sulfonyl chloride and triethylamine in tetrahydrofuran in the presence of an excess of lithium chloride or lithium bromide gives the halide 21. The reaction of 21 with a large excess of a nitrogen containing heterocycle, a sulfide, thiourea, or a phosphine in an inert solvent such as toluene at 50°-150° C. gives the compounds of this invention represented by formula 22a. These compounds are obtained as salts except when A is an imidazole moiety. In those cases where the compounds contain an imidazole ring (formula 22b), the imidazole moiety can be further alkylated with an excess of alkyl halide by heating in an inert solvent such as toluene to give the salts 22e.

In those cases where Q" is tetrahydropyranyl (formula 23), the tetrahydropyranyl group can be hydrolyzed using a hydrochloric acid-tetrahydrofuran mixture. The resulting alcohols 24 are useful to prepare the esters 25 of this invention by refluxing 24 with an excess of the anhydride 26 in the presence of an excess of an amine base such as triethylamine in an inert solvent such as chloroform.

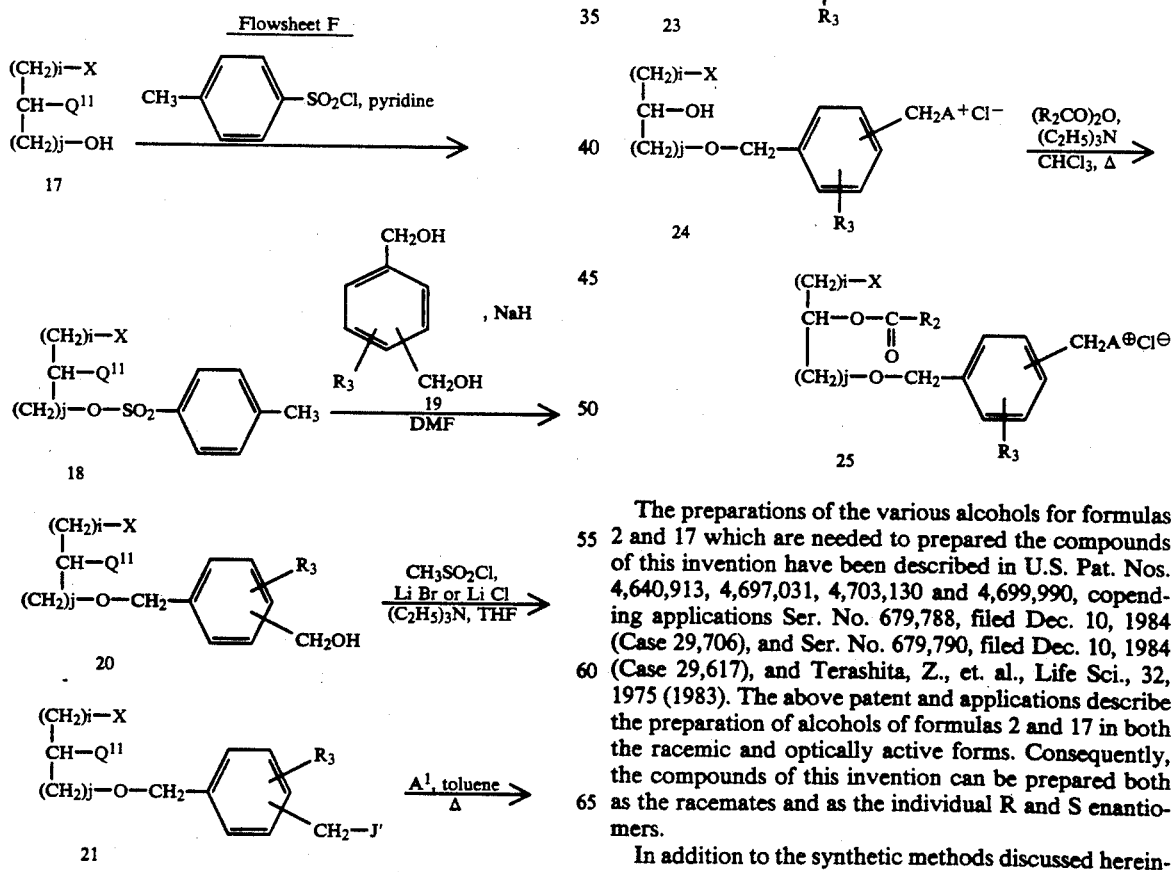
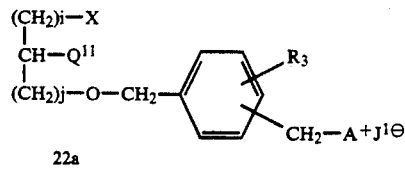
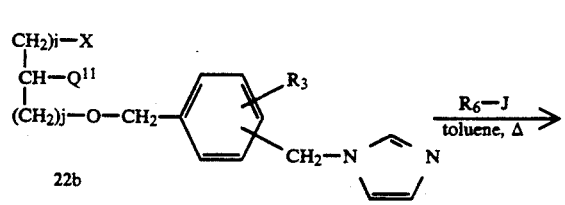
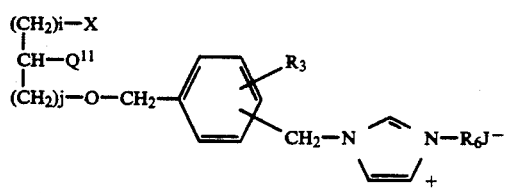
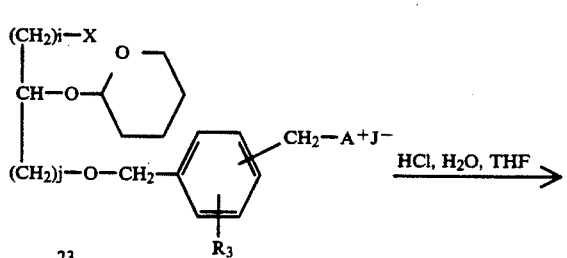
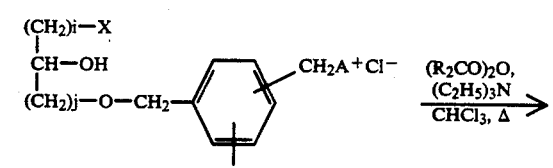
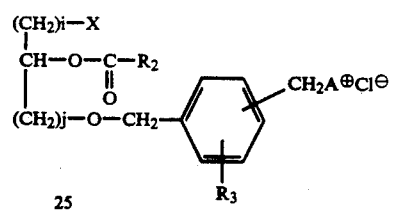

The preparations of the various alcohols for formulas 2 and 17 which are needed to prepared the compounds of this invention have been described in U.S. Pat. Nos. 4,640,913, 4,697,031, 4,703,130 and 4,699,990, copending applications Ser. No. 679,788, filed Dec. 10, 1984 (Case 29,706), and Ser. No. 679,790, filed Dec. 10, 1984 (Case 29,617), and Terashita, Z., et. al., Life Sci., 32, 1975 (1983). The above patent and applications describe the preparation of alcohols of formulas 2 and 17 in both the racemic and optically active forms. Consequently, the compounds of this invention can be prepared both as the racemates and as the individual R and S enantiomers.

In addition to the synthetic methods discussed hereinabove, many of the methods and procedures described in the aforementioned U.S. Patent and copending applications are applicable to the preparation of the compounds of this invention by one skilled in the art.

The compounds were tested for pharmacological activity as described in the following tests.

Platelet Activating Factor Antagonism in vitro

Platelet activating factor (PAF) compounds were evaluated as PAF receptor antagonists in vitro by measuring inhibition of PAF induced platelet aggregation. Platelet aggregation was measured by a modification of the method of A. Wissner, et. al., J. Med. Chem., 27, 1174, 1984.

Approximately 120–240 ml of blood were collected by cardiac puncture from unanesthetized male New Zealand White rabbits (Whaley's Summit View Farms, Belvedere, N.J.) with the use of 3.2% sodium citrate anticoagulant (1 part of citrate/10 parts of blood). All syringes and pipets were plastic. The blood was gently mixed and immediately centrifuged at 800 rpm for 10 minutes at room temperature to recover the platelet rich plasma (PRP). Platelet poor plasma (PPP) was prepared by centrifuging PRP at 2800 rpm for 10 minutes at room temperature.

Dilutions (1:3000) of PRP in Isoton diluent were made and platelet counts were determined on a Coulter Thrombocounter which was standardized with platelet reference standards (Interscience Platelet Control, Portland, Oreg.). PRP platelet counts were adjusted to 500,000 platelets/$\mu$l by the addition of PPP.

L-PAF was obtained from Calbiochem. A stock solution of 1-2 E-3M was prepared in 10% ethanol in water and serial working dilutions were made using phosphate buffered saline (PBS). 1-2 E-3M stock solutions of test compounds were prepared in 100% methanol and serially diluted in PBS. All solutions were made up in plastic tubes, stored on ice and protected from heat and light. Solutions were prepared fresh or frozen at −20° C. and used within 48 hours.

Incubation mixtures consisted of 400 $\mu$l PRP, 50 $\mu$l of PBS diluent or test compound and 50 $\mu$l of PAF agonist. More specifically, 400 $\mu$l of PRP was stabilized in a cuvette for 1–2 minutes at 37° C. in the aggregometer to achieve a stable baseline, then 50 $\mu$l of PBS or test compound, was added and incubated for 5 minutes before addition of the challenge concentration of PAF (final concentration of 5E-8M or 1E-7M, as determined from the dose response curve for PAF for that experiment). Aggregation was monitored for 5 minutes. Samples containing test compound or diluent were run simultaneously for comparison. Test compounds were initially evaluated at a screening concentration of 1E-5M. Those producing $\geq$50% inhibition of the magnitude of aggregation were then reevaluated in a dose response fashion (final concentrations 1E-7M to 5E-5M) and IC50 values were determined.

$K_i$ values were also calculated in some cases from $$K_i = \frac{IC_{50}}{1 + \frac{[PAF]}{EC_{50}}}$$

where
$K_i$ = inhibitory constant
$IC_{50}$ = molar concentration of test compound which gives 50% inhibition
[PAF] = molar concentration of PAF used as challenges
$EC_{50}$ = molar concentration of PAF which gives 50% of maximal aggregation.

The recording equipment consisted of single or dual channel Chronolog aggregometers connected to dual channel 10MV full scale deflection Omniscribe chart recorders (Houston Instruments). The chart recorders were calibrated daily with the use of a suspension of Bio-Rad latex beads (S-X 12 400 mesh) which had a density slightly greater than rabbit PRP. The bead suspension was used to set the 0% light transmission mark and clear water was used to set the 100% light transmission mark. These limits defined a full scale deflection. The aggregation traces were analyzed by a digitizing method (C. Kohler and B. Zoltan, J. Pharm. Methods, 12, 113, 1984) with x, y coordinate data stored in a computer file. A suitable program computed parameters of interest such as the magnitude of aggregation.

In some experiments, washed platelets were used instead of PRP. Washed platelet suspensions were prepared as follows. PRP was centrifuged at 2800 rpm for 10 minutes to obtain PPP and a platelet pellet. The pellet was gently suspended and washed in calcium free, albumin free Tyrode's buffer, pH 6.3. The suspension was recentrifuged and the washed pellet was resuspended in normal Tyrodes' buffer (with calcium, but albumin free), pH 7.4. Platelet counts were adjusted to 500,00 platelets/$\mu$l.

The results of this test on representative compounds of this invention appear in Table I, II, and III.

TABLE I

Inhibition of PAF-Induced Platelet Aggregation in Platelet Rich Plasma

| Compound | IC$_{50}$ (M)* PRP | | |
|---|---|---|---|
| | PAF** 5E-8M | PAF** 1E-7M | PAF** 1E-6M |
| 3-[[[3-[3-(Dodecyloxy)-2-methylphenoxy]-2-methoxypropoxy]hydroxyphosphinyl]oxy]-N,N,N-trimethylbenzenemethanaminium, hydroxide inner salt | 6.0E-6(1)*** | | |
| 3-[[[3-(Hexadecyloxy)-2-methoxypropoxy]-hydroxyphosphinyl]oxy]-N,N,N,-trimethyl-benzenemethanaminium, hydroxide, inner salt | 3.5E-4(1) | | |
| 3-[[3-[[[3-(Hexadecyloxy)-2-methoxyprop-oxy]-hydroxyphosphinyl]oxy]phenyl]-methyl]thiazolium, hydroxide, inner salt | 9.9E-7(3) | 1.0E-6(2) | 4.7E-5(1) |
| 3-[[3-[[[3-[3-Dodecyloxy)-2-methylphen-oxy]-2-methoxypropoxy]hydroxyphosphin-yl]oxy]phenyl]methyl]thiazolium, hydroxide, inner salt | 2.3E-6(3) | 1.9E-6(1) | 2.4E-5(1) |

TABLE I-continued
Inhibition of PAF-Induced Platelet Aggregation in Platelet Rich Plasma

| Compound | IC$_{50}$ (M)* PRP | | |
|---|---|---|---|
| | PAF** 5E-8M | PAF** 1E-7M | PAF** 1E-6M |
| 1-[[3-[[[3-(Hexadecyloxy)-2-methoxypropoxy]-hydroxyphosphinyl]oxy]-phenyl]-methyl]pyridinium hydroxide, inner salt | 5.7E-6(3) | 1.0E-5(1) | 1.8E-4(1) |
| 1-[[3-[[[3-(Dodecyloxy)-2-methylphenoxy]2-methoxypropoxy]hydroxyphosphinyl]oxy]phenyl]methyl]pyridinium, hydroxide, inner salt | 1.7E-7(1) | | |
| 3-[[3-[(1-Hydroxy-4-methoxy-2,6,9,12-tetraoxa-1-phosphadocos-1-yl)oxy]-phenyl]methyl]thiazolium, hydroxide, inner salt, P-oxide | 8.3E-6(2) | | |
| 2-[[3-[[[3-(Hexadecyloxy-2-methoxyphenoxy]hydroxyphosphinyl]oxy]phenyl]methyl]-isoquinolinium hydroxide, inner salt | 2.3E-5(1) | | |
| 3-[[3-[[Hydroxy(octadecyloxy)phosphinyl]oxy]phenyl]methyl]thiazolium, hydroxide, inner salt | 2.2E-5(1) | | |
| 1-[[3-[[Hydroxy(octadecyloxy)phosphinyl]oxy]phenyl]methyl]pyridinium, hydroxide, inner salt | 4.2E-5(3) | | |
| [[3-[[[3-Hexadecyloxy)-2-methoxypropoxy]-hydroxyphosphinyl]oxy]phenyl]methyl]-dimethylsulfoninum, hydroxide, inner salt | 1.3E-5(1) | | |
| [[3-[[[3-(Hexacyloxy)-2-methoxypropoxy]hydroxyphosphinyl]oxy]phenyl]-methyl]triphenylphosphonium, bromide | 1.4E-5(1) | | |
| [[3-[[3-Hydroxy-[2-methoxy-3-(3-tetradecylphenoxy)propoxy]phosphinyl]oxy]-phenyl]methyl]thiazolium, hydroxide, inner salt | 8.1E-7(3) | 9.5E-7(1) | 4.0E-6(1) |
| 1-[[3-[[Hydroxy-[2-methoxy-3-(3-tetradecylphenoxy)propoxy]phosphinyl]-oxy]phenyl]methyl]pyridinium, hydroxide, inner salt | 4.1E-6(3) | 5.4E-6(2) | 5.3E-5(1) |
| [[3-[[Hydroxy-[2-methoxy-3-(3-tetradecylphenoxy)propoxy]phosphinyl]oxy]-phenyl]methyl]dimethylsulfonium, hydroxide, inner salt | 3.4E-6(1) | 2.9E-5(1) | |
| 3-[[3-[1-(Hydroxy-4-methoxy-7-oxo-2,6-dioxa-8-aza-1-phosphahexacosyl)oxy]-phenyl]methyl]thiazolium, hydroxide, inner salt, P-oxide | 1.0E-6(3) | 1.6E-6(1) | 1.7E-5(1) |
| 3-[1-(Hydroxy-4-methoxy-7-oxo-2,6-dioxa-8-aza-1-phosphahexacosyl)oxy]-N,N,N,-trimethylbenzenemethanaminium, hydroxide, inner salt, P-oxide | 1.0E-4(1) | | |
| 3-[[3-[(1-Hydroxy-4-methoxy-7-oxo-2,6-dioxa-8-aza-1-phosphahexacosyl)oxy]-phenyl]methyl]pyridinium, hydroxide, inner salt, P-oxide | 4.4E-6(1) | | |
| 3-[[3-[[3-(Hexadecyloxy)-2-methoxypropoxy]carbonyl]phenyl]methyl]thiazolium, bromide | 3.6E-6(3) | 6.1E-6(2) | 4.9E-5(2) |
| 1-[[3-[[3-(Hexadecyloxy)-2-methoxypropoxy]carbonyl]phenyl]methyl]pyridazinium, bromide | 1.1E-5(1) | | |
| 3-[[3-(Hexadecyloxy)-2-methoxypropoxy]-carbonyl]-N,N,N-trimethylbenzenemethanaminium, bromide | 3.1E-5(1) | 3.0E-5(1) | |
| 3-[[3-[[[Hydroxy-2-methoxy-3-[4-(phenylmethoxy)phenoxy]propoxy]phosphinyl]oxy]-phenyl]methyl]thiazolium, hydroxide, inner salt | 3.3E-5(2) | | |
| 3-[[3-[[[3-[[4-[(4-Chlorophenyl)-methoxy]phenyl]methoxy]2-methoxypropoxy]hydroxyphosphinyl]oxy]phenyl]-methyl]thiazoliu, hydroxide, inner salt | 3.0E-5(2) | | |
| 3-[[3-[[[3-(Hexadecyloxy)-2-methoxypropoxy]hydroxyphosphinyl]oxy]phenyl]-methyl]-5-methylthiazolium, hydroxide, inner salt | 8.2E-7(3) | 7.1E-7(2) | 1.2E-5(1) |
| 3-[[2-[[3-(Hexadecyloxy)-2-methoxypropoxy]hydroxyphosphinyl]oxy]phenyl]- | 5.9E-6(1) | | |

TABLE I-continued
Inhibition of PAF-Induced Platelet Aggregation in Platelet Rich Plasma

| Compound | IC₅₀ (M)* PRP | | |
|---|---|---|---|
| | PAF** 5E-8M | PAF** 1E-7M | PAF** 1E-6M |
| methyl]thiazolium, hydroxide, inner salt | | | |
| 3-[[2-[[[3-[3-(Dodecyloxy)-2-methylphenoxy]2-methoxypropoxy]hydroxyphosphinyl]oxy]phenyl]-methyl]thiazolium, hydroxide, inner salt | 3.3E-6(1) | | |
| 3-[[2-[1-Hydroxy-4-methoxy-7-oxo-2,6-dioxa-8-aza-1-phosphahexacosyl)oxy]-oxy]phenyl]methyl]thiazolium, hydroxide, inner salt P-oxide | 5.6E-7(3) | 1.4E-6(1) | 2.5E-5(1) |
| 3-[[3-[[1-Hydroxy-4-methoxy-2,6,9,12-tetraoxa-1-phosphahexacosyl)oxy]-phenyl]methyl]-5-methylthiazolium, hydroxide, inner salt, P-oxide | 2.2E-6(2) | 3.9E-6(1) | 9.4E-5(1) |
| 3-[[3-[[[3-(Dodecyloxy)-2-methylphenoxy]-2-methoxypropoxy]hydroxyphosphinyl]oxy]phenyl]methyl]-5-methylthiazolium, hydroxide, inner salt | 9.3E-7(1) | 2.0E-6(2) | 3.0E-5(1) |
| 3-[[3-[[[3-(Hexadecyloxy)-2-methoxypropoxy]hydroxyphosphinyl]oxy]phenyl]-methyl]4,5-dimethylthiazolium, hydroxide, inner salt | 1.3E-6(1) | | |
| 1-[[3-[[[3-(Hexadecyloxy)-2-[(2-methyl-2-propenyl)oxy]propoxy]hydroxyphosphinyl]oxy]phenyl]methyl]thiazolium, hydroxide, inner salt | 2.1E-6(1) | 2.6E-6(2) | 3.9E-5(1) |
| 3-[[[3-(Hexadecyloxy)-2-[(2-methyl-2-propeny)oxy]propoxy]hydroxyphosphinyl]-oxy]-N,N,N-trimethylbenzenemethanaminium, hydroxide, inner salt | | 4.8E-5(1) | |
| 3-[[3-[[3-(Hexadecyloxy)-2-methoxypropoxy]hydroxyphosphinyl]phenyl]methyl]-2-(2-methylpropyl)thiazolium, hydroxide, inner salt | 5.3E-6(1) | | |
| 3-[[3-[[[3-[[4-(Dodecyloxy)-1-naphthalenyl]oxy]-2-methoxypropoxy]hydroxyphosphinyl]oxy]phenyl]methyl]thiazolium, hydroxide, inner salt | 3.8E6(1) | | |
| 3-[[2-[[[3-(Hexadecyloxy)-2-[(2-methyl-2-propenyl)oxy]propoxy]hydroxyphosphinyl]oxy]phenylmethyl]thiazolium, hydroxide, inner salt | 2.6E-6(1) | | |
| 3-[[3-[[3-(Hexadecyloxy)-2-methoxypropoxy]methyl]phenyl]methyl]thiazolium, bromide | 1.3E-6(2) | 3.7E-6(2) | 2.6E-5(1) |
| 1-[[3-[[3-(Hexadecyloxy)-2-methoxypropoxy]methyl]phenyl]methyl]-3-methyl-1H-imidazolium, iodide | 3.4E-6(2) | | |
| 1-[[3-[[3-Hexadecyloxy)-2-methoxypropoxy]methyl]phenyl]methyl]1H-imidazole | 5.8E-5(1) | | |
| 3-(Hexadecyloxy)-2-methoxypropylphosphoric acid, 3-(1H-imidazol-1-ylmethyl)phenylester | 1.6E-4(1) | 3.2E-5(1) | |
| 1-[[3-[[[3-[3-(Dodecyloxy)-2-methylphenoxy]-2-methoxypropoxy]hydrophosphinyl]-oxy]phenyl]methyl]quinolinium, hydroxide, inner salt | 7.3E-5(2) | 1.2E-5(1) | |
| 1-[[3-[[3-(Hexadecyloxy)-2-methoxypropoxy]hydroxyphosphinyl]oxy]phenyl]-methyl-3-methyl-1H-imidazolium, hydroxide, inner salt | 9.3E-6(1) | 4.2E-6(1) | |
| 3-[[3-[[Hydroxy[[5-(phenylmethoxy)-2-methoxypentyl]oxy]phosphinyl]oxy]-phenyl]methyl]thiazolium, hydroxide, inner salt | 1.0E-4(1) | | |
| 3-[[3-[[[3-[3-(Dodecyloxy)-2-methylphenoxy]-2-methoxypropoxy]hydroxyphosphinyl]oxy]phenyl]methyl]-5-(2-hydroxyethyl)-4-methylthiazolium, hydroxide, inner salt | 1.7E-5(1) | | |
| 3-[[3-[[Hydroxy-[2-methoxy-3-(4-tetradecylphenoxy)propoxy]phosphinyl]oxy]-phenyl]methyl]thiazolium, hydroxide, inner salt | 2.9E-6(1) | | |
| 3-[[3-[[[2-[(Hexadecyloxy)methyl]-3- | 4.8E-5(1) | 1.3E-4(1) | |

TABLE I-continued
Inhibition of PAF-Induced Platelet Aggregation in Platelet Rich Plasma

| Compound | IC$_{50}$ (M)* PRP | | |
|---|---|---|---|
| | PAF** 5E-8M | PAF** 1E-7M | PAF** 1E-6M |
| [(1-oxooctadecyl)amino]propoxy]hydroxyphosphinyl]oxy]phenyl]methyl]thiazolium, hydroxide, inner salt | | | |
| 3-[[3-[[[3-[[8-([1,1'-Biphenyl]-4-yloxy]octyl]oxy]-2-methoxypropoxy]hydroxyphosphinyl]oxy]phenyl]methyl]thiazolium, hydroxide, inner salt | | 2.3E-6(1) | |
| 3-[[3-[[Hydroxy[2-methoxy-3-[[4-(phenylmethoxy)phenyl]methoxy]propoxy]phosphinyl]oxy]phenyl]methyl]thiazolium, hydroxide, inner salt | 4.0E-4(1) | | |
| 3-[[3-[[[3-[3-(dodecyloxy)-2-methylphenoxy]-2-ethoxypropoxy]hydroxyphosphinyl]oxy]phenyl]methyl]-5-methyl-thiazaolium, hydroxide, inner salt. | | 6.7E-7(2) | |

*Molar IC$_{50}$ values (Concentration which produces 50% inhibition) in rabbit platelet rich plasma.
**Molar challenge concentration of $^1$PAF, platelet activating factor.
***Numbers in parentheses refer to number of experiments.

TABLE II
Inhibition of PAF Induced Platelet Aggregation in Washed Rabbit Platelets

| Compound | IC$_{50}$ (M)* Washed Platelets |
|---|---|
| 3-[[3-[[[3-(Hexadecyloxy)-2-methoxypropoxy]hydroxyphosphinyl]oxy]phenyl]methyl]thiazolium, hydroxide, inner salt | 1.7E-8(1)** |
| [[3-[[3-Hydroxy-[2-methoxy-3-(3-tetradecylphenoxy)propoxy]phosphinyl]oxy]phenyl]methyl]thiazolium, hydroxide, inner salt | 9.5E-9(1) |
| 3-[[3-[1-(Hydroxy-4-methoxy-7-oxo-2,6-dioxa-8-aza-1-phosphahexacosyl)oxy]phenyl]methyl]thiazolium, hydroxide, inner salt, P-oxide | 5.0E-8(1) |
| 3-[[3-[[[3-(Hexadecyloxy)-2-methoxypropoxy]hydroxyphosphinyl]oxy]phenyl]-methyl]-5-methylthiazolium, hydroxide, inner salt | 3.2E-8(1) |
| 3-[[2-[1-(Hydroxy-4-methoxy-7-oxo-2,6-dioxa-8-aza-1-phosphahexacosyl)oxy]phenyl]methyl]thiazolium, hydroxide, inner salt, P-oxide | 5.2E-8(1) |
| 1-[[3-[[3-(Hexadecyloxy)-2-methoxypropoxy]methyl]phenyl]methyl]-3-methyl-1H-imidazolium, iodide | 1.5E-6(1) |

*Molar IC$_{50}$ value (concentration which produces 50% inhibition) in washed rabbit platelets. Challenge concentration of PAF was 5E-9M.
**Numbers in parentheses refer to number of experiments.

TABLE III
In vitro Ki Values for Test Compounds in Rabbit Platelet Platelet Rich Plasma and Washed Pellets

| Compound | Ki (Platelet Rich Plasma) | Ki (Washed Platelets) |
|---|---|---|
| 3-[[3-[[[3-Hexadecyloxy)-2-methoxypropoxy]hydroxyphosphinyl]oxy]phenyl]methyl]thiazolium, hydroxide, inner salt | 4.9E-7 | 8.0E-9 |
| 3-[[3-[[[3-[3-(Dodecyloxy)-2-methyphenoxy]-2-methoxypropoxy]hydroxyphosphinyl]oxy]phenyl]methyl]thiazolium, hydroxide, inner salt | 5.1E-7 | |
| [[3-[[3-Hydroxy-[2-methoxy-3-(3-tetradecylphenoxy)propoxy]phosphinyl]oxy]phenyl]methyl]thiazolium, hydroxide, inner salt | 2.1E-7 | 1.4E-9 |
| 3-[[3-[1-Hydroxy-4-methoxy-7-oxo-2,6-dioxa-8-aza-1-phosphahexacosyl)oxy]phenyl]methyl]thiazolium, hydroxide, inner salt, P-oxide | 3.2E-7 | 7.5E-9 |
| 3-[[3-[[[3-Hexadecyloxy)-2-methoxypropoxy]hydroxyphosphinyl]oxy]phenyl]methyl]-5-methylthiazolium, hydroxide, inner salt | 2.1E-7 | 1.5E-8 |
| 3-[[2-[(1-Hydroxy-4-methoxy-7-oxo-2,6-dioxa-8-aza-1-phosphahexacosyl)oxy]phenyl]methyl]thiazolium, hydroxide, inner salt, P-oxide | 3.1E-7 | 7.2E-9 | where $Ki = \frac{IC_{50}}{1 + ([PAF]/EC_{50})}$

IC$_{50}$ = Molar concentration of test compound which gives 50% inhibition.
[PAF] = Molar concentration of PAF used as challenge agonist.
EC$_{50}$ = Molar concentration for PAF to induce 50% of maximal aggregation response in controls.

Inhibition of PAF Induced Vascular Permeability Change in Guinea Pig Skin

Platelet Activating Factor (PAF) given intradermally, increases capillary permeability, and plasma proteins (e.g. albumin) leak from the vascular space into the interstitial fluids of the skin. If the albumin has been previously stained with Evans' blue dye, the lesion area can be visualized as a blue spot in the skin. A specific PAF antagonist inhibits the development of increased capillary permeability caused by PAF and reduces the leakage of proteins into the skin. Test compounds were evaluated for non-specific effects by monitoring their ability to inhibit or reduce a histamine induced increase in capillary permeability.

Test Solutions were prepared as follows: Evans' Blue Dye (Sigma E2129) was dissolved in saline to yield a 0.1% w/v solution. A 2 mg/ml stock chloroform solution of PAF (1-phosphotidyl, acetyl-O-alkyl; Sigma P9525) was diluted in saline to give final concentrations of 500 and 250 ng/ml. Saline dilutions were made fresh for each test. Histamine diphosphate solutions (Sigma H7375) were prepared by dissolving 10 mg in 100 ml of saline and diluting to 20 μg/ml with saline. Test compounds were dissolved in ethanol at 10 mg/ml and stored at −70° C. Injection mixtures were made by placing 10 μl of test compound solution into 1.0 ml of either the PAF solutions or the histamine solution.

The animals used were Hartley strain guinea pigs weighing 250-350 g, maintained with food and water ad libitum. The animals were shaved on their back and hind feet one day before use.

Each guinea pig was given an intravenous injection of 2 ml of Evans' blue dye solution into a foot vein. Immediately after, a series of six intradermal injections of 0.1 ml each were given, three on each side of the animal. They were: PAF 50 ng (0.1 ml of a 500 ng/ml solution); PAF 25 ng; and histamine diphosphate 2 μg. The left side injections contain 10 μg of test compound while the right side contain an equivalent amount of the ethanol vehicle to serve as a control.

Thirty minutes later the animals were killed by cervical dislocation and the skin reflected from the back. The lesion areas were approximated as the product of the largest diameter and normal diameter both in mm.

A test compound was considered active if it caused a 50% or greater reduction in the lesion area of the PAF injection which produced a control lesion closest to 100 mm$^2$ without altering the histamine induced spot. The results appear in Table IV.

Inhibition of PAF Induced Vascular Permeability Change in Mouse Skin

The rationale for this test is similar to the coinjection test in guinea pigs; however, the test compound was given intraperitoneally rather than coinjected.

Test solutions were prepared as follows: An 80 μg portion of PAF was dissolved in 40 ml of saline to yield a concentration of 2000 ng/ml. A 10 mg portion of histamine diphosphate was dissolved in 100 ml of saline to yield a concentration 100 μg/ml. Test compounds were dissolved in saline and given intraperitoneally (20 mg/kg) ½ hour before intradermal challenge with PAF or histamine.

The animals used were Hilltop ICR mice, shaved on their flanks one day before use. The mice were randomly assigned to treated and control groups and were given test compound or saline ½ hour before challenge. Each mouse was injected via a tail vein with 0.25 ml of 0.05% Evans' blue dye immediately before the PAF or histamine intradermal injections were made (0.05 ml each), one per side.

Thirty minutes later the animals were killed and the lesions areas measured as described above. Lesion areas in treated animals were expressed as a percent of the control lesions and an ED$_{50}$ (mg/kg) was calculated from an arcsine area vs. log dose transform. The results appear in Table IV.

PAF Induced Lethality in the Mouse

Test compounds were evaluated for their ability to prevent death induced by an intravenous injection of a lethal dose of PAF.

ICR mice were given test compounds intraperitoneally as described under Inhibition of PAF Induced Vascular Permeability Change in Mouse Skin, ½ hour before an intravenous dose of 100 μg/kg PAF in saline. One hour later the number of dead mice were recorded. Protection was expressed as percent survivors in treated group/percent survivors in control group. The results appear in Table IV.

TABLE IV

| Compound | Inhibition of* Vascular Permeability Lesion (% of Control) | Inhibition of** Vascular Permeability Lesion (ED$_{50}$ mg/kg) | PAF Induced*** Lethality PD$_{50}$ (mg/kg I.P., ½ hour) |
|---|---|---|---|
| 3-[[[3-[[Hydroxy-2-methoxy-3-[4-(phenyl-methoxy)phenoxy]propoxy]phosphinyl]oxy]-phenyl]methyl]thiazolium, hydroxide, inner salt | 67 | 20 | <25 |
| 3-[[3-[[[3-(Hexadecylocy)-2-methoxypropoxy]hydroxyphosphinyl]oxy]phenyl]methyl]-5-methylthiazoliu, hydroxide, inner salt | 24 | 4.8 | <1.25 |
| 3-[[2-[(1-Hydroxy-4-methoxy-7-oxo-2,6-dioxa-8-aza-1-phosphahexacosyl)oxy]-phenyl]methyl]thiazolium, hydroxide, inner salt, P-oxide | 25 | 5 | <2.5 |
| 3-[[3-[[[3-(Hexadecyloxy)-2-methoxypropoxy]hydroxyphosphinyl]oxy]phenyl]-methyl]thiazolium, hydroxide, inner salt | 25 | 5.6 | <1.25 |
| 3-[[3-[[[3[3-(Dodecyloxy)-2-methyl-phenoxy]-2-methoxypropoxy]hydroxyphosphinyl]oxy]phenyl]methyl]thiazolium, hydroxide, inner salt | 20.4 | 8.2 | <1.25 |
| [[3-[[3-Hydroxy-[2-methoxy-3-(3-tetra-decylphenoxy)propoxy]phosphinyl]oxy]-phenyl]methyl]thiazolium, hydroxide, inner salt | 3.8 | 5.3 | <1.25 |
| 3-[[3-[(1-Hydroxy-4-methoxy-7-oxo-2,6-dioxa-8-aza-1-phosphahexacosyl)oxy]-phenyl]methyl]thiazolium, hydroxide, inner salt, P-oxide | 61.8 | 6.2 | |

*Guinea pig skin; test compounds (10 g) and PAF challenge given intradermally.
**Mouse skin; test compounds given i.p. and PAF challenge given i.d.
***Mice; test compounds given i.p. and PAF challenge given i.v. Values are that dose that protects ½ the animals = PD$_{50}$.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 1 and 250 mg of active compound.

The tablets, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of this invention may also be administered directly to the airways in the form of an aeresol.

The invention will be further described by the following examples.

EXAMPLE 1

3-(Bromomethyl)phenyl phosphodichlorodate

A 9.1 g portion of 99% phosphorous tribromide, 10 ml of carbon tetrachloride and 1.32 ml of dry pyridine in 2.5 ml of tetrahydrofuran was reacted with 12.41 g of 4-hydroxybenzyl alcohol in 100 ml of dry tetrahydrofuran containing 0.7 ml of pyridine. The intermediate 4-hydroxybenzyl bromide was treated with phosphorous oxychloride, giving 5.6 g of the desired compound.

EXAMPLE 2

2-Chloro-4H-1,3,2-benzodioxaphosphorin, 2-oxide

To a solution of 100 g of hydroxybenzyl alcohol and 121.69 g of phosphorous trichloride in 1000 ml of ether at −10° C., was added dropwise a solution of 133.81 g of pyridine in 200 ml of ether over 1.5 hours. The mixture was stirred for 1.5 hours at room temperature and then refrigerated overnight. The mixture was filtered, the solvent removed, hexane added, the mixture filtered and the solvent removed. The residue was distilled via a Kugelrohr (1 mm 80°-90° C.) giving 81 g of a colorless liquid. A solution of this material in benzene was stirred and oxygen bubbled in for 20 hours, then the benzene was removed, giving 87.5 g of the desired compound as a yellow liquid.

EXAMPLE 3

3-[[2-[(1-Hydroxy-4-methoxy-7-oxo-2,6-dioxa-8-aza-1-phosphahexacosyl)oxy]phenyl]methyl]thiazolium, hydroxide, inner salt, P-oxide A mixture of 225 g of glycerol, 259.28 g of benzaldehyde and 4.5 g of p-toluensulfonic acid was stirred under argon at reflux in toluene using a Dean-Stark trap for 5 hours, then cooled to 0° C. and 200 ml of petroleum ether added with stirring. The mixture was stored at 0° C. overnight, then the solid was collected, washed with petroleum ether and dissolved in 1300 ml of toluene. Enough sodium methoxide was added to neutralize the p-toluensulfonic acid, then the solution was washed with 1 liter of 1% disodium phosphate, dried and cooled to 0° C. After 2 hours the 145 g of white solid was collected, washed with petroleum ether and dried. A 125 g portion of this solid in 400 ml of dimethylformamide was added to a suspension of 39.94 g of 50 g of sodium hydride in 200 ml of dimethylformamide under argon over 1 hour. The mixture was cooled to 0° C. and 147.69 g of methyl iodide in 100 ml of dimethylformamide was added over 1 hour. The mixture was stirred at room temperature overnight, then water was added and the mixture extracted with ether. The extract was dried, the solvent evaporated and the residue crystallized from carbon tetrachloride/hexane, giving 60 g of off-white solid. A 50 g portion of this solid in 100 ml of ether was added over 15 minutes to 146.14 g of borontrifluoride etherate in 200 ml of ether under argon, to which had been added at 0° C., with stirring, a suspension of 10.26 g of lithium aluminium hydride in 800 ml of ether. This mixture was stirred at room temperature for 1 hour, then at reflux for 4.5 hours, then at room temperature overnight. A 500 ml portion of 10% sulfuric acid was added slowly. The ether layer was separated, washed with sodium bicarbonate, dried and evaporated to an oil. This oil was purified by chromatography, giving 27.58 g of a colorless oil. A 15 g portion of this oil, 22.59 g of n-octadecylisocyanate and 50 ml of pyridine was allowed to stand overnight, then poured into water and extracted with ether. The extract was washed with dilute hydrochloric acid, then dried and evaporated to an oil. The oil was crystallized from methanol/water, giving 35 g of white solid. A mixture of 30 g of this solid 3 g of 5% palladium on carbon, 120 ml of glacial acetic acid and 125 ml of methanol were hydrogenated in a Parr apparatus for 18 hours, then 10 drops of concentrated hydrochloric acid were added and hydrogenolysis continued for 3 hours. The mixture was filtered, the filtrate extracted with chloroform, the extract washed with sodium bicarbonate, dried, and evaporated. The residue was crystallized from hexane, giving 21 g of white solid, referred to as (A) in future examples.

To a solution of 2.2 g of the above solid (A) and 1.23 g of 2-chloro-4H-1,3,2-benzodioxaphosphorin, 2-oxide in 25 ml of carbon tetrachloride was added 665 mg of triethylamine. The mixture was stirred overnight, filtered through diatomaceous earth and evaporated. The residue was combined with 5.6 g of thiazole and 140 ml of toluene and heated at 90° C. for 3 days. The solvent was removed and the residue purified by chromatography, giving 0.9 g of the desired product as a foam.

EXAMPLE 4

3-[[3-[(1-Hydroxy-4-methoxy-7-oxo-2,6-dioxa-8-aza-1-phosphahexacosyl)oxy]phenyl]methyl]thiazolium, hydroxide, inner salt P-oxide A solution of 5 g of the solid (A) from Example 3 in 60 ml of carbon tetrachloride was treated under argon with a solution of 4.54 g of 3-(3-bromomethyl)phenyl phosphodichlorodate in 10 ml of carbon tetrachloride. This mixture was cooled in an ice bath and treated with a solution of 2.1 ml of triethylamine in 10 ml of carbon tetrachloride. The mixture was stirred at room temperature for 18 hours and then evaporated. The residue was added to a mixture of 130 ml of tetrahydrofuran and 130 ml of 0.5N sodium acetate and stirred for 1.5 hours. The tetrahydrofuran was removed, the aqueous remainder acidified with dilute hydrochloric acid and extracted three times with ether. The extracts were combined, washed with brine, dried and evaporated. The residue was purified by chromatography, giving 4.23 g of 3-[[[3-(bromomethyl)phenoxy]hydroxyphosphinyl]oxy]octadecylcarbamic acid-2-methoxypropyl ester as a glass.

A 2 portion of the above ester and 2.09 g of thiazole was stirred in 15 ml of toluene, under argon at 65°-70° C. for 18 hours, then allowed to stand at room temperature and evaporated. The residue was stirred with 2 g of Amberlite,IR-B4 ion exchange resin in 50 ml of methanol for 2 hours, then filtered and evaporated. The residue was purified by chromatography, giving 1.62 g of the desired product as a glass.

EXAMPLE 5

3-[[3-[(1-Hydroxy-4-methoxy-7-oxo-2,6-dioxa-8-aza-1-phosphahexacosyl)oxy]phenyl]methyl]pyridinium, hydroxide, inner salt, P-oxide A mixture of 1 g of 3-[[[3-(bromomethyl)phenoxy]hydroxyphosphinyl]oxy]oxtadecycarbamic acid-2-methoxypropyl ester and 973 mg of pyridine in 15 ml of toluene was stirred at 65°-70° C. for 18 hours and then evaporated. The residue was stirred with 1 g of methanol washed Amberlite,IR-B4 ion exchange resin for 1.5 hours, then filtered and evaporated. The residue was purified by chromatography and then triturated with ether, giving 880 mg of the desired product as a white amorphous solid.

According to the methods described in detail hereinabove in Examples 3, 4 and 5, the compounds of this invention listed hereinbelow in Table V can be prepared using the appropriate nitrogen containing heterocycle, phosphorous reagent and alcohol. The alcohols are obtained as described in detail in the U.S. Pat. Nos. 4,640,913, 4,697,031, 4,703,130 and 4,699,990 and our copending applications, and the following reference: Terashita z., et al, Life Sci. 32, 1975 (1983). The compounds of this invention can be prepared as the individual optically active R and S enantiomers or as the racemic mixtures as described in the formentioned patents and applications.

TABLE V

3-[[3-[(1-hydroxy-4-methoxy-7-oxo-2,6-dioxa-8-aza-1-phosphahexacosyl)oxy]phenyl]methyl]thiazolium, hydroxide, inner salt, P-oxide 3-[[3-[(1-hydroxy-4-methoxy-7-oxo-2,6-dioxa-8-aza-1-phosphahexacosyl)oxy]phenyl]methyl]-4,5-dimethylthiazolium, hydroxide, inner salt, P-oxide 3-[[3-[(1-hydroxy-4-methoxy-7-oxo-2,6-dioxa-8-aza-1-phosphahexacosyl)oxy]phenyl]methyl]-5-methylthiazolium, hydroxide, inner salt, P-oxide 3-[[3-[(1-hydroxy-4-methoxy-7-oxo-2,6-dioxa-8-aza-1-phosphatetracosyl)oxy]phenyl]methyl]thiazolium, hydroxide, inner salt, P-oxide 3-[[3-[(1-hydroxy-4-methoxy-7-oxo-2,6-dioxa-8-aza-1-phosphatetracosyl)oxy]phenyl]methyl]-4,5-dimethylthiazolium, hydroxide, inner salt, P-oxide 3-[[3-[(1-hydroxy-4-methoxy-7-oxo-2,6-dioxa-8-aza-1-phosphatetracosyl)oxy]phenyl]methyl]-5-methylthiazolium, hydroxide, inner salt, P-oxide 3-[[3-[(1-hydroxy-4-ethoxy-7-oxo-2,6-dioxa-8-aza-1-phosphahexacosyl)oxy]phenyl]methyl]thiazolium, hydroxide, inner salt, P-oxide 3-[[3-[(1-hydroxy-4-ethoxy-7-oxo-2,6-dioxa-8-aza-1-phosphatetracosyl)oxy]phenyl]methyl]thiazolium, hydroxide, inner salt, P-oxide 3-[[3-[(1-hydroxy-4-isopropoxy-7-oxo-2,6-dioxa-8-aza-1-phosphahexacosyl)oxy]phenyl]methyl]thiazolium, hydroxide, inner salt, P-oxide 3-[[3-[(1-hydroxy-4-isopropoxy-7-oxo-2,6-dioxa-8-aza-1-phosphahexacosyl)oxy]phenyl]methyl]-4,5-dimethylthiazolium, hydroxide, inner salt, P-oxide 3-[[3-[(1-hydroxy-4-isopropoxy-7-oxo-2,6-dioxa-8-aza-1-phosphahexacosyl)oxy]phenyl]methyl]-5-methylthiazolium, hydroxide, inner salt, P-oxide 3-[[3-[(1-hydroxy-4-isopropoxy-7-oxo-2,6-dioxa-8-aza-1-phosphatetracosyl)oxy]phenyl]methyl]thiazolium, hydroxide, inner salt, P-oxide 3-[[3-[(1-hydroxy-4-isopropoxy-7-oxo-2,6-dioxa-8-aza-1-phosphatetracosyl)oxy]phenyl]methyl]-4,5-dimethylthiazolium, hydroxide, inner salt, P-oxide 3-[[3-[(1-hydroxy-4-isopropoxy-7-oxo-2,6-dioxa-8-aza-1-phosphatetracosyl)oxy]phenyl]methyl]-5-methylthiazolium, hydroxide, inner salt, P-oxide 3-[[2-[(1-hydroxy-4-methoxy-7-oxo-2,6-dioxa-8-aza-1-phosphahexacosyl)oxy]phenyl]methyl]thiazolium, hydroxide, inner salt, P-oxide 3-[[2-[(1-hydroxy-4-methoxy-7-oxo-2,6-dioxa-8-aza-1-phosphahexacosyl)oxy]phenyl]methyl]-4,5-dimethylthiazolium, hydroxide, inner salt, P-oxide 3-[[2-[(1-hydroxy-4-methoxy-7-oxo-2,6-dioxa-8-aza-1-phosphahexacosyl)oxy]phenyl]methyl]-5-methylthiazolium, hydroxide, inner salt, P-oxide 3-[[2-[(1-hydroxy-4-methoxy-7-oxo-2,6-dioxa-8-aza-1-phosphatetracosyl)oxy]phenyl]methyl]thiazolium, hydroxide, inner salt, P-oxide 3-[[2-[(1-hydroxy-4-methoxy-7-oxo-2,6-dioxa-8-aza-1-phosphatetracosyl)oxy]phenyl]methyl]-4,5-dimethylthiazolium, hydroxide, inner salt, P-oxide 3-[[2-[(1-hydroxy-4-methoxy-7-oxo-2,6-dioxa-8-aza-1-phosphatetracosyl)oxy]phenyl]methyl]-5-methylthiazolium, hydroxide, inner salt, P-oxide 3-[[2-[(1-hydroxy-4-ethoxy-7-oxo-2,6-dioxa-8-aza-1-phosphahexacosyl)oxy]phenyl]methyl]thiazolium, hydroxide, inner salt, P-oxide 3-[[2-[(1-hydroxy-4-ethoxy-7-oxo-2,6-dioxa-8-aza-1-phosphatetracosyl)oxy]phenyl]methyl]thiazolium, hydroxide, inner salt, P-oxide 3-[[4-[(1-hydroxy-4-methoxy-7-oxo-2,6-dioxa-8-aza-1-phosphahexacosyl)oxy]phenyl]methyl]thiazolium, hydroxide, inner salt, P-oxide 3-[[4-[(1-hydroxy-4-methoxy-7-oxo-2,6-dioxa-8-aza-1-phosphahexacosyl)oxy]phenyl]methyl]-4,5-dimethylthiazolium, hydroxide, inner salt, P-oxide 3-[[4-[(1-hydroxy-4-methoxy-7-oxo-2,6-dioxa-8-aza-1-phosphahexacosyl)oxy]phenyl]methyl]-5-methylthiazolium, hydroxide, inner salt, P-oxide 3-[[4-[(1-hydroxy-4-methoxy-7-oxo-2,6-dioxa-8-aza-1-phosphatetracosyl)oxy]phenyl]methyl]thiazolium, hydroxide, inner salt, P-oxide 3-[[4-[(1-hydroxy-4-methoxy-7-oxo-2,6-dioxa-8-aza-1-phosphatetracosyl)oxy]phenyl]methyl]-4,5-dimethylthiazolium, hydroxide, inner salt, P-oxide 3-[[4-[(1-hydroxy-4-methoxy-7-oxo-2,6-dioxa-8-aza-1-phosphatetracosyl)oxy]phenyl]methyl]-5-methylthiazolium, hydroxide, inner salt, P-oxide 3-[[4-[(1-hydroxy-4-isopropoxy-7-oxo-2,6-dioxa-8-aza-1-phosphahexacosyl)oxy]phenyl]methyl]thiazolium, hydroxide, inner salt, P-oxide 3-[[4-[(1-hydroxy-4-isopropoxy-7-oxo-2,6-dioxa-8-aza-1-phosphahexacosyl)oxy]phenyl]methyl]-4,5-dimethylthiazolium, hydroxide, inner salt, P-oxide 3-[[4-[(1-hydroxy-4-isopropoxy-7-oxo-2,6-dioxa-8-aza-1-phosphahexacosyl)oxy]phenyl]methyl]-5-methylthiazolium, hydroxide, inner salt, P-oxide 3-[[4-[(1-hydroxy-4-isopropoxy-7-oxo-2,6-dioxa-8-aza-1-phosphatetracosyl)oxy]phenyl]methyl]thiazolium, hydroxide, inner salt, P-oxide 3-[[4-[(1-hydroxy-4-isopropoxy-7-oxo-2,6-dioxa-8-aza-1-phosphatetracosyl)oxy]phenyl]methyl]-4,5-dimethylthiazolium, hydroxide, inner salt, P-oxide 3-[[4-[(1-hydroxy-4-isopropoxy-7-oxo-2,6-dioxa-8-aza-1-phosphatetracosyl)oxy]phenyl]methyl]-5-methylthiazolium, hydroxide, inner salt, P-oxide 1-[[3-[(1-hydroxy-4-methoxy-7-oxo-2,6-dioxa-8-aza-1-phosphahexacosyl)oxy]phenyl]methyl]pyridinium, hydroxide, inner salt, P-oxide 1-[[3-[(1-hydroxy-4-methoxy-7-oxo-2,6-dioxa-8-aza-1-phosphahexacosyl)oxy]phenyl]methyl]quinolinium, hydroxide, inner salt, P-oxide 1-[[3-[(1-hydroxy-4-methoxy-7-oxo-2,6-dioxa-8-aza-1-phosphatetracosyl)oxy]phenyl]methyl]pyridinium, hydroxide, inner salt, P-oxide 1-[[3-[(1-hydroxy-4-methoxy-7-oxo-2,6-dioxa-8-aza-1-phosphatetracosyl)oxy]phenyl]methyl]quinolinium, hydroxide, inner salt, P-oxide 1-[[3-[(1-hydroxy-4-ethoxy-7-oxo-2,6-dioxa-8-aza-1-phosphahexacosyl)oxy]phenyl]methyl]pyridinium, hydroxide, inner salt, P-oxide 1-[[3-[(1-hydroxy-4-ethoxy-7-oxo-2,6-dioxa-8-aza-1-phosphahexacosyl)oxy]phenyl]methyl]quinolinium, hydroxide, inner salt, P-oxide 1-[[3-[(1-hydroxy-4-ethoxy-7-oxo-2,6-dioxa-8-aza-1-phosphatetracosyl)oxy]phenyl]methyl]pyridinium, hydroxide, inner salt, P-oxide 1-[[3-[(1-hydroxy-4-ethoxy-7-oxo-2,6-dioxa-8-aza-1-phosphatetracosyl)oxy]phenyl]methyl]quinolinium, hydroxide, inner salt, P-oxide 1-[[3-[(1-hydroxy-4-isopropoxy-7-oxo-2,6-dioxa-8-aza-1-phosphahexacosyl)oxy]phenyl]methyl]pyridinium, hydroxide, inner salt, P-oxide 1-[[3-[(1-hydroxy-4-isopropoxy-7-oxo-2,6-dioxa-8-aza-1-phosphahexacosyl)oxy]phenyl]methyl]quinolinium, hydroxide, inner salt, P-oxide 1-[[3-[(1-hydroxy-4-isopropoxy-7-oxo-2,6-dioxa-8-aza-1-phosphatetracosyl)oxy]phenyl]methyl]pyridinium, hydroxide, inner salt, P-oxide 1-[[3-[(1-hydroxy-4-isopropoxy-7-oxo-2,6-dioxa-8-aza-1-phosphatetracosyl)oxy]phenyl]methyl]quinolinium, hydroxide, inner salt, P-oxide 1-[[2-[(1-hydroxy-4-methoxy-7-oxo-2,6-dioxa-8-aza-1-phosphahexacosyl)oxy]phenyl]methyl]pyridinium, hydroxide, inner salt, P-oxide 1-[[2-[(1-hydroxy-4-methoxy-7-oxo-2,6-dioxa-8-aza-1-phosphahexacosyl)oxy]phenyl]methyl]quinolinium, hydroxide, inner salt, P-oxide 1-[[2-[(1-hydroxy-4-methoxy-7-oxo-2,6-dioxa-8-aza-1-phosphatetracosyl)oxy]phenyl]methyl]pyridinium, hydroxide, inner salt, P-oxide 1-[[2-[(1-hydroxy-4-methoxy-7-oxo-2,6-dioxa-8-aza-1-phosphatetracosyl)oxy]phenyl]methyl]quinolinium, hydroxide, inner salt, P-oxide 1-[[2-[(1-hydroxy-4-ethoxy-7-oxo-2,6-dioxa-8-aza-1-phosphahexacosyl)oxy]phenyl]methyl]pyridinium, hydroxide, inner salt, P-oxide 1-[[2-[(1-hydroxy-4-ethoxy-7-oxo-2,6-dioxa-8-aza-1-phosphahexacosyl)oxy]phenyl]methyl]quinolinium, hydroxide, inner salt, P-oxide 1-[[2-[(1-hydroxy-4-ethoxy-7-oxo-2,6-dioxa-8-aza-1-phosphatetracosyl)oxy]phenyl]methyl]pyridinium, hydroxide, inner salt, P-oxide 1-[[2-[(1-hydroxy-4-ethoxy-7-oxo-2,6-dioxa-8-aza-1-phosphatetracosyl)oxy]phenyl]methyl]quinolinium, hydroxide, inner salt, P-oxide 1-[[4-[(1-hydroxy-4-methoxy-7-oxo-2,6-dioxa-8-aza-1-phosphahexacosyl)oxy]phenyl]methyl]pyridinium, hydroxide, inner salt, P-oxide 1-[[4-[(1-hydroxy-4-methoxy-7-oxo-2,6-dioxa-8-aza-1-phosphahexacosyl)oxy]phenyl]methyl]quinolinium, hydroxide, inner salt, P-oxide 1-[[4-[(1-hydroxy-4-methoxy-7-oxo-2,6-dioxa-8-aza-1-phosphatetracosyl)oxy]phenyl]methyl]pyridinium, hydroxide, inner salt, P-oxide 1-[[4-[(1-hydroxy-4-methoxy-7-oxo-2,6-dioxa-8-aza-1-phosphatetracosyl)oxy]phenyl]methyl]quinolinium, hydroxide, inner salt, P-oxide 1-[[4-[(1-hydroxy-4-isopropoxy-7-oxo-2,6-dioxa-8-aza-1-phosphahexacosyl)oxy]phenyl]methyl]pyridinium, hydroxide, inner salt, P-oxide 1-[[4-[(1-hydroxy-4-isopropoxy-7-oxo-2,6-dioxa-8-aza-1-phosphahexacosyl)oxy]phenyl]methyl]quinolinium, hydroxide, inner salt, P-oxide 1-[[4-[(1-hydroxy-4-isopropoxy-7-oxo-2,6-dioxa-8-aza-1-phosphatetracosyl)oxy]phenyl]methyl]pyridinium, hydroxide, inner salt, P-oxide 1-[[4-[(1-hydroxy-4-isopropoxy-7-oxo-2,6-dioxa-8-aza-1-phosphatetracosyl)oxy]phenyl]methyl]quinolinium, hydroxide, inner salt, P-oxide

EXAMPLE 6

3-[[3-[[Hydroxy-2-methoxy-3-[4-(phenylmethoxy)phenoxy]propoxy]phosphinyl]oxy]phenyl]methyl]thiazolium, hydroxide, inner salt To mixture of 15.6 g of 3-[4-(phenylmethoxy)phenoxy]-1,2-propanediol in 30 ml of dry pyridine, cooled in a water bath under argon was added dropwise at a fast rate a solution of 21.95 g of p-methoxy trityl chloride in 90 ml of dry tetrahydrofuran. The resulting solution was stirred for 1 hour, refrigerated for 48 hours, then stirred at room temperature for 6 hours, filtered and washed with ether. The filtrate was evaporated, water was added and the mixture extracted twice with ether. The extracts were combined washed with water and brine, dried and evaporated to dryness, giving a syrup.

This syrup was dissolved in 180 ml of dimethylformamide and 65 ml of tetrahydrofuran and added dropwise to a mixture of 4.09 g of hexane washed 50% sodium hydride in 65 ml of dimethylformamide containing 24.21 g of methyl iodide over a 45 minute period, under argon, while cooled in an ice bath. The mixture was stirred overnight at room temperature, then refrigerated. Ice was added followed by 500 ml of ice-water. This mixture was extracted twice with ether. The extracts were combined, washed with water, dried and evaporated. The residual gum was dissolved in a boiling mixture of 180 ml of methanol and 90 ml of chloroform and 18 g of Amberlyst ® 15 ion exchange resin was added. This mixture was stirred for 1.5 hours, then filtered and the filtrate evaporated to dryness. The residue was dissolved in methanol, then taken to dryness and purified by chromatography, giving 5.4 g of 2-methoxy-3-[4-(phenylmethoxy)phenoxy]-1-propanol.

A 3 g portion of 2-methoxy-3-[4-(phenylmethoxy)phenoxy]-1-propanol in 30 ml of carbon tetrachloride was reacted with 3.79 g of 3-(bromomethyl)phenyl phosphodichlorodate in 7 ml of carbon tetrachloride at 0° C. A 1.26 g portion of triethylamine in 10 ml of carbon tetrachloride was added and this mixture was stirred at room temperature for 18 hours. The solvent was removed and the residue hydrolyzed in 80 ml of tetrahydrofuran and 80 ml of 0.5M sodium acetate for 2 hours. The tetrahydrofuran was evaporated and the aqueous remainder acidified and extracted twice with ether. The extracts were combined, washed with brine, dried and evaporated. The residue was purified by chromatography, giving 2.95 g of 3-(bromomethyl)phenyl-2-methoxy-3-[4-(phenylmethoxy)phenoxy]phosphoric acid, propyl ester as hard glass.

A 1.5 g portion of the above propyl ester and 1.9 g of thiazole in 15 ml of toluene were stirred for 18 hours in a 65°-70° C. oil bath under argon and then evaporated. The residue was stirred with 1.5 g of Amberlite ® IR-4B ion exchange resin in 40 ml of methanol for 2 hours, then filtered and the filtrate evaporated. The residue was purified by chromatography, giving 1.26 g of the desired product as a white amorphous powder.

EXAMPLE 7

[[3-[[3-[[Hydroxy[2-methoxy-3-(3-tetradecylphenoxy)-propoxy]phosphinyl]oxy]phenyl]methyl]thiazolium, hydroxide inner salt To a solution of 9.2 g of 2-methoxy-3-(3-tetradecylphenoxy)-1-propanol in 110 ml of dry carbon tetrachloride was added dropwise a solution of 8.9 g of 3-(bromomethyl)phenyl phosphodichlorodate in 20 ml of carbon tetrachloride. This mixture was cooled in an ice bath and a solution of 2.96 g of triethylamine in 20 ml carbon tetrachloride was added dropwise. This mixture was stirred under argon at room temperature overnight and then filtered. The filtrate was evaporated and the residue hydrolyzed in a mixture of 250 ml of tetrahydrofuran and 250 ml of 0.5M sodium acetate for 2 hours. The tetrahydrofuran was removed, the aqueous phase acidified and extracted three times with ether. The extracts were combined, washed with saturated sodium chloride, dried and evaporated. The residue was purified by chromatography, giving 7.33 g of 3-(bromomethyl)phenyl-3-(3-tetradecylphenoxy)phosphoric acid-2-methoxypropyl ester.

To a solution of 2 g of the above ester in 15 ml of dry toluene was added 1.8 ml of thiazole. This solution was stirred overnight in an oil bath at 65°-70° C. under argon and then evaporated. The residue was dissolved in 50 ml of methanol and stirred with 2 g of methanol washed Amberlite ® IR-4B ion exchange resin for 1 hour, then filtered, washed with methanol and the combined filtrate and wash evaporated. The residue was purified by chromatography, giving 1.538 g of the desired product as a buff colored glass.

EXAMPLE 8

3-[[3-[[[3-[3-(Dodecyloxy)-2-methylphenoxy]-2-methoxypropoxy]hydroxyphosphinyl]oxy]phenyl]methyl]-5-methylthiazolium, hydroxide, inner salt To a stirred mixture of 2.98 g of hexane washed sodium hydride in 160 ml of dry dimethylformamide was added 17.6 g of methyl iodide, followed by the dropwise addition of a solution of 26.5 g of 1-[3-(dodecyloxy)-2-methylphenoxy]-3-[(4-methoxyphenyl)diphenylmethoxy]-2-propanol in 55 ml of dimethylformamide and 55 ml of dry tetrahydrofuran over 1 hour. This mixture was stirred overnight, then ice was added followed by 500 ml of cold water. The mixture was extracted twice with ether, the extracts combined, washed with water, dried and evaporated. The residue was hydrolyzed in 160 ml of methanol, 80 ml of chloroform and 16 g of Amberlite ® IR-4B ion exchange resin, giving 26.7 of an oil. This oil was purified by chromatography, giving 11.3 g of an oil; referred to as (B) in future examples.

To a solution of 4 g of the above oil in 60 ml of carbon tetrachloride was added a solution of 4.47 g of 3-(bromomethyl)phenyl phosphodichlorodate in 10 ml of carbon tetrachloride. This mixture was cooled and stirred under argon in an ice bath as 1.49 g of triethylamine in 10 ml of carbon tetrachloride was added. This mixture was stirred at room temperature for 4 hours, then filtered and evaporated. The residue was stirred in a mixture of 130 ml of tetrahydrofuran and 130 ml of 0.5M sodium acetate for 2 hours, hours, then the tetrahyudrofuran was removed. The aqueous remainder was acidified with hydrochloric acid and extracted three times with ether. The extracts were combined, washed with brine, dried and evaporated. The residue was purified by chromatography, giving 5.13 g of 3-(bromomethyl)phenyl-3-[3-(dodecyloxy)-2-methylphenoxy]phosphoric acid-2-methoxypropyl ester.

A solution of 1.45 g of the above ester in 15 ml of toluene was treated with 1.14 g of 5-methylthiazole at 65° C. under argon for 18 hours and then evaporated. The residue was dissolved 40 ml of methanol and stirred at room temperature for 2 hours with 1.5 g of methanol washed Amberlite ® IR-4B ion exchange resin, then filtered and evaporated. The residue was purified by chromatography and then triturated with ether, giving 970 mg of the desired compound as a hard glass.

EXAMPLE 9

3-[[[3-[3-(Dodecyloxy)-2-methylphenoxy]-2-methoxypropoxy]hydroxyphosphinyl]oxy]-N,N,N-trimethylbenzenemethanaminum, hydroxide, inner salt To a solution of 2 g of 3-(bromomethyl)phenyl-3-[3-(dodecyloxy)-2-methylphenoxy]phosphoric acid-2-methoxypropyl ester in 60 ml of dry chloroform was added 40 ml of a solution of 50 g of trithylamine in 100 ml dry of acetonitrile. The solution was stirred at reflux for 4 hours and then stirred overnight at room temperature. The solvent was removed and the residue taken up in a mixture of 25 ml of methanol, 25 ml of chloroform and 1 ml of water and stirred with 447 mg of silver carbonate for 2 hours. The mixture was filtered, washed with methanol:chloroform (1:1). The solvent was removed, the residue triturated with ether and then purified by chromatography, giving 1.17 g of the desired product as a white powder.

EXAMPLE 10

3-[[3-[[[3-[3-(Dodecyloxy)-2-methylphenoxy]-2-methoxypropoxy]hydroxyphosphinyl]oxy]phenyl]methyl]thiazolium, hydroxide, inner salt To a solution of 2 g of 3-(bromomethyl)phenyl-3-[3-(dodecyloxy)-2-methylphenoxy]phosphoric acid-2-methoxypropyl ester in 15 ml of dry toluene stirred under argon at 65°-70° C. in an oil bath, was added 1.9 ml of thiazole. The mixture was stirred at 65°-70° C. for 18 hours and then evaporated. The residue was dissolved in 50 ml of methanol and stirred with 2 g of methanol washed Amberlite® IR-4B ion exchange resin under argon for 1 hour. The mixture was filtered, washed with methanol and evaporated. The residue was purified by chromatography, giving 1.8 g of the desired product as a buff-colored glass.

EXAMPLE 11

3-[[2-[[[3-[3-(Dodecyloxy)-2-methylphenoxy]-2-methoxypropoxy]hydroxyphosphinyl]oxy]phenyl]methyl]thiazolium, hydroxide, inner salt To a solution of 2.23 g of the oil (B) from Example 8 and 1.2 g of 2-chloro-4H-1,3,2-benzodioxaphosphorin, 2-oxide in 25 ml of carbon tetrachloride was added 683 mg of triethylamine. This mixture was stirred overnight, then filtered and evaporated. The residue was dissolved in 30 ml of toluene containing 5.99 g of thiazole under argon and heated at 80°-90° C. for 3 days. The solvent was removed and the residue purified by chromatography giving the desired product as a thick oil.

EXAMPLE 12

1-[[3-[[[3-[3-(Dodecyloxy)-2-methylphenoxy]-2-methoxypropoxy]hydroxyphosphinyl]oxy]phenyl]methyl]quinolinium, hydroxide, inner salt A solution of 1.54 g of 3-(bromomethyl)phenyl-3-[3-(dodecyloxy)-2-methylphenoxy]phosphoric acid-2-methoxypropyl ester and 2.53 g of quinoline in 15 ml of dry toluene was stirred overnight in a 65° C. oil bath under argon and then evaporated. The residual oil was stirred with 1.8 g of methanol washed Amberlite® IR-4B ion exchange resin in 45 ml of methanol for 2 hours and then evaporated. The residue was purified by chromatography, gaining 964 mg of the desired product as a hard buff-colored glass.

EXAMPLE 13

3-[[3-[[[3-[[4-[(4-Chlorophenyl)methoxy]phenyl]methoxy]-2-methoxypropoxy]hydroxyphosphinyl]oxy]phenyl]methyl]thiazolium, hydroxide, inner salt To a solution of 2 g of 3-[[4-[(4-chlorophenyl)methoxy]phenyl]methoxy]-2-methoxy-1-propanol in 20 ml of carbon tetrachloride was added 2.17 g of 3-(bromomethyl)phenyl phosphodichlorodate in 5 ml of carbon tetrachloride. The mixture was cooled in an ice bath and 721 mg of triethylamine in 5 ml of carbon tetrachloride was added dropwise. The mixture was stirred at room temperature for 4 hours, refrigerated 48 hours, filtered, washed with carbon tetrachloride and evaporated. The residue was stirred in a mixture of 50 ml of tetrahydrofuran and 50 ml of 0.5M sodium acetate for 2 hours, then the tetrahydrofuran was removed, the aqueous remainder acidified with hydrochloric acid and ice bath cooling and extracted twice with ether. The extracts were combined, dried and evaporated. The residue was purified by chromatography giving 1.92 g of 3-(bromomethyl)phenylphosphoric acid, 3-[[4-[(4-chlorophenyl)methoxy]phenyl]methoxy]-2-methoxypropyl ester.

To 1.9 g of the above ester in 15 ml of toluene was added 2.27 g of thiazole. This solution was stirred at 65° C.-70° C. under argon for 18 hours then evaporated. The residue was stirred with 1.5 g of Amberlite® IR-4B ion exchange resin in 40 ml of methanol for 2 hours, then filtered and evaporated. The residue was purified by chromatography, then triturated with ether and refrigerated, giving 1.61 g of the desired product as a white amorphous powder.

EXAMPLE 14

3-[[3-[[[3-[3-(Dodecyloxy)-2-methylphenoxy]-2-methoxypropoxy]hydroxyphosphinyl]oxy]phenyl]methyl]-5-(2-hydroxyethyl)-4-methylthiazolium, hydroxide, inner salt A mixture of 2 g of 3-(bromomethyl)phenyl-3-[3-(dodecyloxy)-2-methylphenoxy]phosphoric acid-2-methoxypropyl ester and 3.64 g of 4-methyl-5-thiazolethanol in 20 ml of toluene was stirred under argon at 65° C. in an oil bath for 18 hours and then evaporated. The residue was stirred with 2 g of Amberlite® IR-4B ion exchange resin in 60 ml of methanol for 2 hours, then filtered and evaporated. The residue was purified by chromatography, giving 1.8 g of the desired product as a buff-colored hard glass.

EXAMPLE 15

1-[[3-[[[3-[3-(Dodecyloxy)-2-methylphenoxy]-2-methoxypropoxy]hydroxyphosphinyl]oxy]phenyl]methyl]pyridinium, hydroxide, inner salt To a solution of 2 g of 3-(bromomethyl)phenyl-3-[3-(dodecyloxy)-2-methylphenoxy]phosphoric acid-2-methoxypropyl ester in 15 ml of dry toluene was added 2.2 ml of dry pyridine. This mixture was stirred under argon in an oil bath at 60°-65° C. for 17 hours, then allowed to cool to room temperature and stirred for 48 hours. The solvent was removed and the residue dissolved in 50 ml of methanol. A 2 g portion of methanol washed Amberlite® IR-4B ion exchange resin was added and this mixture stirred for 1 hour, then filtered, washed with methanol and evaporated. The residue was purified by chromatography, giving 1.6 g of the desired product as a glass.

EXAMPLE 16

3-[[3-[[[3-[[4-(Dodecyloxy)-1-naphthalenyl]oxy]-2-methoxypropoxy]hydroxyphosphinyl]oxy]phenyl]methyl]thiazolium, hydroxide, inner salt To a stirred washed suspension of 3.65 g of sodium hydride in 60 ml of dimethylformamide under argon was added a solution of 20 g of 4-(dodecyloxy)-1-naphthalenol in 80 ml of tetrahydrofuran followed by 0.91 g of sodium iodide and 14.81 g of solketal mesylate. The mixture was heated at 80° C. for 8 hours, then stirred at room temperature overnight. Water was added and the mixture extracted with ether. The extract was evaporated, the residue refluxed in a mixture of 200 ml of methanol, 32 ml of water and 2 ml of sulfuric acid and then evaporated. The residue was dissolved in chloroform, washed with water, dried, filtered and evaporated. The residue was crystallized from methanol, giving 21 g of 3-[[4-(dodecyloxy)-1-naphthalenyl]oxy]-1,2-propanediol as a white solid.

A solution of 3.5 g of the above diol, 3.36 g of p-methoxytrityl chloride, 9.5 ml of pyridine and 25 ml of tetrahydrofuran was stirred overnight, then 200 ml of iced water was added and the mixture extracted three times with ether. The extracts were combined, washed with water, dried and evaporated. The residue was evaporated twice from toluene, giving an oil.

To a mixture of 626 mg of hexane washed 50% sodium hydride in 40 ml of dimethylformamide stirred under argon, was added 3.7 g of methyl iodide and a solution of 5.87 g of the above oil in 15 ml of dimethylformamide and 15 ml of tetrahydrofuran. This mixture was stirred for 4 hours, then quenched with ice and water and extracted twice with ether. The extracts were combined, washed with water and evaporated. The residue was dissolved in 40 ml of chloroform and 80 ml of methanol, brought to a boil, 5 g of Amberlite® IR-4B ion exchange resin added and this mixture stirred for 2 hours, then filtered and evaporated. The residue was taken up in methanol, refrigerated for 48 hours and then evaporated. The residue was purified by chromatography, giving 2.5 g of 3-[[4-(dodecyloxy)-1-naphthalenyl]oxy]-2-methoxy-1-propanol. To a solution of 2.45 g of 3-[[4-(dodecyloxy)-1-naphthalenyl]oxy]-2-methoxy-1-propanol in 30 ml of carbon tetrachloride, cooled in an ice bath under argon, was added with stirring 2.5 g of 3-(bromomethyl)phenyl phosphodichlorodate in 5 ml of carbon tetrachloride. To this was added dropwise a solution of 869 mg of triethylamine in 5 ml of carbon tetrachloride. This mixture was stirred overnight then filtered and evaporated. The residue was stirred in a mixture of 60 ml of tetrahydrofuran and 60 ml of 0.5M sodium acetate for 2 hours, then the tetrahydrofuran was removed. The aqueous remainder was acidified with hydrochloric acid and extracted twice with ether. The extracts were combined, washed with brine, dried and evaporated. The residue was purified by chromatography, giving 1.86 g of 3-bromomethyl)phenyl-3-[[4-(dodecyloxy)-1-naphthalenyl]oxy]phosphoric acid-2-methoxypropyl ester as a glass.

A mixture of 1.8 g of the above ester, 1.84 g of thiazole and 15 ml of toluene was stirred at 68° C. for 24 hours and then evaporated. The residue was added to a solution of 2 g of Amberlite® IR-4B ion exchange resin in 50 ml of methanol, stirred for 2 hours, then filtered and evaporated. The residue was purified by chromatography and crystallized from ether, giving 1.41 g of the desired product as an amorphous white powder.

EXAMPLE 17

1-[[3-[[Hydroxy[2-methoxy-3-(3-tetradecylphenoxy)-propoxy]phosphinyl]oxy]phenyl]methyl]pyridinium, hydroxide, inner salt To a solution of 1 g of 3-(bromomethyl)phenyl-3-(3-hexadecylphenoxy)phosphoric acid-2-methoxypropyl ester in 10 ml of dry toluene was added 1 ml of dry pyridine. This solution was stirred in an oil bath at 65°-70° C. under argon for 18 hours and then evaporated. The residue was dissolved in 50 ml of methanol and stirred with 2 g of Amberlite® IR-4B ion exchange resin for 2 hours, then filtered, washed with methanol and the solvent removed. The residue was purified by chromatography, giving 944 mg of the desired product as a glass.

EXAMPLE 18

3-[[3-[[Hydroxy[2-methoxy-3-(4-tetradecylphenoxy)-propoxy]phosphinyl]oxy]phenyl]methyl]thiazolium, hydroxide, inner salt To a mixture of 275 mg of 2-methoxy-3-(tetradecylphenoxy)-1-propanol and 309 mg of 3-(bromomethyl)-phenyl phosphodichlorodate in 6 ml of carbon tetrachloride cooled under argon, was added 103 mg of triethylamine in 1 ml of carbon tetrachloride. The mixture was stirred 18 hours and then evaporated. The residue was hydrolyzed in 10 ml of tetrahydrofuran and 10 ml of 0.5M sodium acetate for 2 hours, then the tetrahydrofuran was removed. The aqueous remainder was acidified with hydrochloric acid and extracted twice with ether. The extracts were combined, washed with brine, dried and evaporated. The residue was purified by chromatography, giving 336 mg of 3-(bromomethyl)phenyl-phosphoric 2-methoxy-3-(4-tetradecylphenoxy)propyl ester as glass.

A mixture of 325 mg of the above ester, 353 mg of thiazole and 5 ml of toluene was stirred at 65° C. under argon for 18 hours and then evaporated. The residue was stirred with a mixture of 800 mg of Amberlite® IR-4B ion exchange resin and 10 ml of methanol for 2 hours, then filtered and evaporated. The residue was purified by chromatography and then evaporated twice from ether, giving 276 mg of the desired product as a white amorphous solid.

EXAMPLE 19

3-[[3-[[[3-[[8-([1,1'-Biphenyl]-4-yloxy)octyl]oxy]-2-methyoxypropoxy]hydroxyphosphinyl]oxy]phenyl]methyl]thiazolium, hydroxide, inner salt A solution of 7.6 g of 1-[[8-([1,1'-biphenyl]-4-yloxy)octyl]oxy]-3-[(4-methoxyphenyl)diphenylmethoxy]-2-propanol in 20 ml of dimethylformamide and 20 ml of tetrahydrofuran was added dropwise to a solution of 849 mg of hexane washed 50% sodium hydride in 50 ml of dimethylformamide containing 5.02 g of methyl iodide over 35 minutes under argon. The mixture was stirred overnight then ice was cautiously added followed by 300 ml of iced water. This mixture was extracted three times with ether, the extracts combined, washed with water, dried and evaporated. The residue was taken up in 65 ml of chloroform and 130 ml of methanol, heated to boiling, 8 g of Amberlite® IR-4B ion exchange resin added, stirred for 2 hours, filtered and evaporated. The residue was purified by chromatography, giving 1.27 g of 3-[[8-([1,1'-biphenyl]-4-yloxy]octyl]oxy]-2-methoxy-1-propanol.

To a solution of 1.1 g of the above compound in 15 ml of carbon tetrachloride was added a solution of 1.21 g of 3-(bromomethyl)phenyl phosphordichlorodate in 5 ml of carbon tetrachloride. With stirring a solution of 403 mg of triethylamine in 5 ml of carbon tetrachloride was added dropwise under argon. The mixture was stirred 4 hours, filtered, rinsed with toluene and evaporated. The residue was stirred in a mixture of 30 ml of tetrahydrofuran and 30 ml of 0.5M sodium acetate for 1 hour then the tetrahydrofuran was removed. The aqueous remainder was acidified with hydrochloric acid and extracted three times with ether. The extracts were combined, washed with brine, dried and evaporated. The residue was purified by chromatography, giving 1.81 g of 3-[[8-([1,1'-biphenyl]-4-yloxy)octyl]oxy]-2-methoxypropylphosphoric acid, 3-(bromomethyl)phenyl ester.

A mixture of 1.35 g of the above ester, 1.45 g of thiazole and 15 ml of toluene was heated at 65° C. under argon for 18 hours and then evaporated. The residue was stirred with 1.5 g of methanol washed Amberlite ® IR-4B ion exchange resin in 40 ml of methanol for 2 hours, then filtered and evaporated. The residue was purified by chromatography, then evaporated once from toluene and twice from ether, giving 1.12 g of the desired product as a buff-colored amorphous solid.

EXAMPLE 20

[[3-[[3-[[Hydroxy[2-methoxy-3-(3-tetradecylphenoxy)-propoxy]phosphinyl]oxy]phenyl]methyl]thiazolium, hydroxide, inner salt To a solution of 2.5 g of 2-methoxy-3-(3-tetradecylphenoxy)-1-propanol in 30 ml of dry carbon tetrachloride was added, with ice bath cooling, 2.8 g of 3-(bromomethyl)phenyl phosphodichlorodate. The mixture was stirred under argon in an ice bath and a solution of 1.3 ml of triethylamine in 5 ml of carbon tetrachloride was added dropwise. This mixture was stirred at room temperature overnight, then filtered and evaporated. The residue was stirred in a mixture of 65 ml of tetrahydrofuran and 65 ml of 0.5M sodium acetate for 2 hours, then the tetrahydrofuran was removed. The aqueous phase was chilled and acidified with concentrated hydrochloric acid, then extracted three times with ether. The extracts were combined, washed with brine and evaporated. The residue was purified by chromatography, giving 715 mg of 3-(bromomethyl)phenyl-3-(3-tetradecylphenoxy)phosphoric acid-2-methoxypropyl ester.

A solution of the above 715 mg and 776 mg of thiazole in 6 ml of dry toluene was stirred at 65° C. under argon for 20 hours and then evaporated. The residue was stirred with 750 mg of Amberlite,IR-4B ion exchange resin in 25 ml of methanol for 2 hours and then evaporated. The residue was washed with methanol, then chromatographed on silica gel, eluting with chloroform:methanol:water (65:35:6), giving 300 mg of the desired product.

According to the methods described in detail hereinabove in Examples 6-20, the compounds of this invention listed hereinbelow in Table VI can be prepared using the appropriate nitrogen containing heterocyle, phosphorous reagent and alcohol. The alcohols are obtained as described in detail in the U.S. Pat. Nos. 4,640,913, 4,697,031, 4,703,130 and 4,699,990 and our copending applications, and the following reference: Terashita z., et al, Life Sci. 32, 1975 (1983). The compounds of this invention can be prepared as the individual optically active R and S enantiomers or as the racemic mixtures as described in the formentioned patents and applications.

TABLE VI

3-[[3-[[[3-[3-(dodecyloxy)-2-methylphenoxy]-2-propoxypropoxy]hydroxyphosphinyl]oxy]phenyl]methyl]-thiazolium, hydroxide, inner salt 3-[[3-[[[3-[2-(dodecyloxy)-phenoxy]-2-methoxypropoxy]hydroxyphosphinyl]oxy]phenyl]methyl]-5-methyl-thiazolium, hydroxide, inner salt 3-[[3-[[[3-[3-(dodecyloxy)-2-methylphenoxy]-2-ethoxypropoxy]hydroxyphosphinyl]oxy]phenyl]methyl]-thiazolium, hydroxide, inner salt 3-[[3-[[[3-[3-(dodecyloxy)-2-methylphenoxy]-2-ethoxypropoxy]hydroxyphosphinyl]oxy]phenyl]methyl]-5-methylthiazolium, hydroxide, inner salt 3-[[3-[[[3-[3-(dodecyloxy)-phenoxy]-2-methoxypropoxy]hydroxyphosphinyl]oxy]phenyl]methyl]-thiazolium, hydroxide, inner salt 3-[[3-[[[3-[3-(dodecyloxy)-phenoxy]-2-methoxypropoxy]hydroxyphosphinyl]oxy]phenyl]methyl]-5-methyl-thiazolium, hydroxide, inner salt 3-[[2-[[[3-[2-(dodecyloxy)-phenoxy]-2-methoxypropoxy]hydroxyphosphinyl]oxy]phenyl]methyl]-thiazolium, hydroxide, inner salt 3-[[3-[[[3-[4-(dodecyloxy)-phenoxy]-2-propoxypropoxy]hydroxyphosphinyl]oxy]phenyl]methyl]-thiazolium, hydroxide, inner salt 3-[[3-[[[3-[2-(dodecyloxy)-phenoxy]-2-methoxypropoxy]hydroxyphosphinyl]oxy]phenyl]methyl]-5-methyl-thiazolium, hydroxide, inner salt 3-[[3-[[[3-[4-(dodecyloxy)-phenoxy]-2-ethoxypropoxy]-hydroxyphosphinyl]oxy]phenyl]methyl]thiazolium, hydroxide, inner salt 3-[[3-[[[3-[4-(dodecyloxy)-phenoxy]-2-ethoxypropoxy]-hydroxyphosphinyl]oxy]phenyl]methyl]-5-methyl-thiazolium, hydroxide, inner salt 3-[[2-[[[3-[2-(tridecyloxy)-phenoxy]-2-methoxypropoxy]hydroxyphosphinyl]oxy]phenyl]methyl]

3-[[2-[[[3-[3-(dodecyloxy)-2-methylphenoxy]-2-methoxypropoxy]hydroxyphosphinyl]oxy]phenyl]methyl]-5-methylthiazolium, hydroxide, inner salt 3-[[2-[[[3-[3-(dodecyloxy)-2-methylphenoxy]-2-ethoxypropoxy]hydroxyphosphinyl]oxy]phenyl]methyl]-thiazolium, hydroxide, inner salt 3-[[2-[[[3-[3-(dodecyloxy)-2-methylphenoxy]-2-ethoxypropoxy]hydroxyphosphinyl]oxy]phenyl]methyl]-5-methylthiazolium, hydroxide, inner salt 3-[[2-[[[3-[3-(dodecyloxy)-phenoxy]-2-methoxypropoxy]hydroxyphosphinyl]oxy]phenyl]methyl]-thiazolium, hydroxide, inner salt 3-[[2-[[[3-[3-(benzyloxy)-phenoxy]-2-ispropoxypropoxy]hydroxyphosphinyl]oxy]phenyl]methyl]-3,5-dimethylthiazolium, hydroxide, inner salt 3-[[4-[[[3-[3-(dodecyloxy)-2-methylphenoxy]-2-methoxypropoxy]hydroxyphosphinyl]oxy]phenyl]methyl]-thiazolium, hydroxide, inner salt 3-[[4-[[[3-[3-(dodecyloxy)-2-methylphenoxy]-2-methoxypropoxy]hydroxyphosphinyl]oxy]phenyl]methyl]-5-methylthiazolium, hydroxide, inner salt 3-[[4-[[[3-[3-(dodecyloxy)-2-methylphenoxy]-2-ethoxypropoxy]hydroxyphosphinyl]oxy]phenyl]methyl]-thiazolium, hydroxide, inner salt 3-[[4-[[[3-[3-(dodecyloxy)-2-methylphenoxy]-2-ethoxypropoxy]hydroxyphosphinyl]oxy]phenyl]methyl]-5-methylthiazolium, hydroxide, inner salt 3-[[4-[[[3-[3-(dodecyloxy)-phenoxy]-2-methoxypropoxy]hydroxyphosphinyl]oxy]phenyl]methyl]-thiazolium, hydroxide, inner salt 3-[[4-[[[3-[3-(dodecyloxy)-phenoxy]-2-methoxypropoxy]hydroxyphosphinyl]oxy]phenyl]methyl]-5-methylthiazolium, hydroxide, inner salt 1-[[3-[[[3-[3-(dodecyloxy)-2-methylphenoxy]-2-methoxypropoxy]hydroxyphosphinyl]oxy]phenyl]methyl]-3-methylpyridinium, hydroxide, inner salt 1-[[3-[[[3-[3-(benzyloxy)-2-methylphenoxy]-2-methoxypropoxy]hydroxyphosphinyl]oxy]phenyl]methyl]-3-ethyl-1H-imidazolium, hydroxide, inner salt 1-[[3-[[[3-[3-(dodecyloxy)-2-methylphenoxy]-2-ethoxypropoxy]hydroxyphosphinyl]oxy]phenyl]methyl]-3-methyl-1H-imidazolium, hydroxide, inner salt 1-[[3-[[[3-[3-(dodecyloxy)-2-methylphenoxy]-2-ethoxypropoxy]hydroxyphosphinyl]oxy]phenyl]methyl]-pyridinium, hydroxide, inner salt 1-[[3-[[[3-[4-(dodecyloxy)-phenoxy]-2-propoxypropoxy]hydroxyphosphinyl]oxy]phenyl]methyl]-3-methyl-1H-imidazolium, hydroxide, inner salt 1-[[2-[[[3-[3-(dodecyloxy)-2-methylphenoxy]-2-methoxypropoxy]hydroxyphosphinyl]oxy]phenyl]methyl]-quinolinium, hydroxide, inner salt 1-[[2-[[[3-[3-(dodecyloxy)-2-methylphenoxy]-2-methoxypropoxy]hydroxyphosphinyl]oxy]phenyl]methyl]-3-propyl-1H-imidazolium, hydroxide, inner salt 1-[[2-[[[3-[3-(dodecyloxy)-2-methylphenoxy]-2-methoxypropoxy]hydroxyphosphinyl]oxy]phenyl]methyl]-3-methyl-1H-imidazolium, hydroxide, inner salt 1-[[2-[[[3-[3-(dodecyloxy)-2-methylphenoxy]-2-isobutoxypropoxy]hydroxyphosphinyl]oxy]phenyl]methyl]quinolinium, hydroxide, inner salt 1-[[2-[[[3-[3-(dodecyloxy)-2-methylphenoxy]-2-ethoxypropoxy]hydroxyphosphinyl]oxy]phenyl]methyl]-3-ethyl-1H-imidazolium, hydroxide, inner salt 1-[[2-[[[3-[3-(dodecyloxy)-2-methylphenoxy]-2-ethoxypropoxy]hydroxyphosphinyl]oxy]phenyl]methyl]-3-methyl-1H-imidazolium, hydroxide, inner salt 1-[[4-[[[3-[3-(dodecyloxy)-2-methylphenoxy]-2-methoxypropoxy]hydroxyphosphinyl]oxy]phenyl]methyl]-pyridinium, hydroxide, inner salt 1-[[4-[[[3-[3-(dodecyloxy)-2-methylphenoxy]-2-methoxypropoxy]hydroxyphosphinyl]oxy]phenyl]methyl]-quinolinium, hydroxide, inner salt 1-[[4-[[[3-[3-(dodecyloxy)-2-methylphenoxy]-2-methoxypropoxy]hydroxyphosphinyl]oxy]phenyl]methyl]-3-propyl-1H-imidazolium, hydroxide, inner salt 1-[[4-[[[3-[3-(dodecyloxy)-2-methylphenoxy]-2-methoxypropoxy]hydroxyphosphinyl]oxy]phenyl]methyl]-3-methyl-1H-imidazolium, hydroxide, inner salt 1-[[4-[[[3-[3-(dodecyloxy)-2-methylphenoxy]-2-ethoxypropoxy]hydroxyphosphinyl]oxy]phenyl]methyl]-pyridinium, hydroxide, inner salt 1-[[4-[[[3-[3-(dodecyloxy)-2-methylphenoxy]-2-ethoxypropoxy]hydroxyphosphinyl]oxy]phenyl]methyl]-quinolinium, hydroxide, inner salt 1-[[4-[[[3-[3-(dodecyloxy)-2-methylphenoxy]-2-ethoxypropoxy]hydroxyphosphinyl]oxy]phenyl]methyl]-3-ethyl-1H-imidazolium, hydroxide, inner salt 1-[[4-[[[3-[3-(dodecyloxy)-2-methylphenoxy]-2-ethoxypropoxy]hydroxyphosphinyl]oxy]phenyl]methyl]-3-methyl-1H-imidazolium, hydroxide, inner salt 3-[[3-[[[3-[3-(dodecyloxy)-phenoxy]-2-methoxypropoxy]hydroxyphosphinyl]oxy]phenyl]methyl]isoquinolinium, hydroxide, inner salt 1-[[3-[[[3-[3-(dodecyloxy)-2-methylphenoxy]-2-methoxypropoxy]hydroxyphosphinyl]oxy]phenyl]methyl]-pyridazinium, hydroxide, inner salt 1-[[3-[[[3-[3-(dodecyloxy)-2-methylphenoxy]-2-methoxypropoxy]hydroxyphosphinyl]oxy]phenyl]methyl]-pyrimidinium, hydroxide, inner salt 1-[[3-[[[3-[3-(dodecyloxy)-2-methylphenoxy]-2-methoxypropoxy]hydroxyphosphinyl]oxy]phenyl]methyl]-pyrazinium, hydroxide, inner salt 3-[[3-[[[3-[[4-(dodecyloxy)-1-naphthalenyl]oxy]-2-methoxypropoxy]hydroxyphosphinyl]oxy]phenyl]methyl]thiazolium, hydroxide, inner salt 3-[[3-[[[3-[[2-(dodecyloxy)-1-naphthalenyl]oxy]-2-methoxypropoxy]hydroxyphosphinyl]oxy]phenyl]methyl]-5-methylthiazolium, hydroxide, inner salt 3-[[3-[[[3-[[4-(benzyloxy)-1-naphthalenyl]oxy]-2-ethoxypropoxy]hydroxyphosphinyl]oxy]phenyl]methyl]thiazolium, hydroxide, inner salt 3-[[3-[[[3-[[3-(tetradecyloxy)-2-naphthalenyl]oxy]-2-methoxypropoxy]hydroxyphosphinyl]oxy]phenyl]methyl]thiazolium, hydroxide, inner salt 3-[[2-[[[3-[[5-(tridecyloxy)-1-naphthalenyl]oxy]-2-methoxypropoxy]hydroxyphosphinyl]oxy]phenyl]methyl]thiazolium, hydroxide, inner salt 3-[[3-[[[3-[[5-(dodecyloxy)-2-naphthalenyl]oxy]-2-methoxypropoxy]hydroxyphosphinyl]oxy]phenyl]methyl]thiazolium, hydroxide, inner salt 3-[[3-[[[3-[[5-(dodecyloxy)-2-naphthalenyl]oxy]-2-methoxypropoxy]hydroxyphosphinyl]oxy]phenyl]methyl]-5-methylthiazolium, hydroxide, inner salt 3-[[3-[[[-3-[[7-(tridecyloxy)-2-naphthalenyl]oxy]-2-ethoxypropoxy]hydroxyphosphinyl]oxy]phenyl]methyl]thiazolium, hydroxide, inner salt 1-[[3-[[hydroxy[2-methoxy-3-(3-tetradecylphenoxy)propoxy]phosphinyl]oxy]phenyl]methyl]-quinolinium, hydroxide, inner salt 1-[[3-[[hydroxy[2-methoxy-3-(3-tetradecylphenoxy)propoxy]phosphinyl]oxy]phenyl]methyl]-1H-imidazolium, hydroxide, inner salt 1-[[3-[[hydroxy[2-methoxy-3-(4-tetradecylphenoxy)propoxy]phosphinyl]oxy]phenyl]methyl]pyridinium, hydroxide, inner salt 1-[[3-[[hydroxy[2-methoxy-3-(3-dodecylphenoxy)propoxy]phosphinyl]oxy]phenyl]methyl]pyridinium, hydroxide, inner salt 3-[[3-[[hydroxy[2-methoxy-3-(3-tetradecylphenoxy)propoxy]phosphinyl]oxy]phenyl]methyl]thiazolium, hydroxide, inner salt 3-[[3-[[hydroxy[2-methoxy-3-(3-tetradecylphenoxy)propoxy]phosphinyl]oxy]phenyl]methyl]-5-methylthiazolium, hydroxide, inner salt 3-[[3-[[hydroxy[2-methoxy-3-(3-tetradecylphenoxy)propoxy]phosphinyl]oxy]phenyl]methyl]-2-(2-methylpropyl)-thiazolium, hydroxide, inner salt 3-[[3-[[hydroxy[2-methoxy-3-(2-pentadecylphenoxy)propoxy]phosphinyl]oxy]phenyl]methyl]thiazolium, hydroxide, inner salt 3-[[3-[[hydroxy[2-methoxy-3-(2-pentadecylphenoxy)propoxy]phosphinyl]oxy]phenyl]methyl]-5-methylthiazolium, hydroxide, inner salt 3-[[3-[[hydroxy[2-methoxy-3-(2-pentadecylphenoxy)propoxy]phosphinyl]oxy]phenyl]methyl]-2-(2-methylpropyl)-thiazolium, hydroxide, inner salt 3-[[3-[[hydroxy[2-propoxy-3-(4-tetradecylphenoxy]-propoxy]phosphinyl]oxy]phenyl]methyl]thiazolium, hydroxide, inner salt 3-[[3-[[hydroxy[2-methoxy-3-(4-tetradecylphenoxy]-propoxy]phosphinyl]oxy]phenyl]methyl]-5-methyl-thiazolium, hydroxide, inner salt 3-[[3-[[hydroxy[2-methoxy-3-(3-dodecylphenoxy]-propoxy]phosphinyl]oxy]phenyl]methyl]thiazolium, hydroxide, inner salt 3-[[3-[[hydroxy[2-methoxy-3-(3-dodecylphenoxy]-propoxy]phosphinyl]oxy]phenyl]methyl]-5-methyl-thiazolium, hydroxide, inner salt 3-[[3-[[hydroxy[2-ethoxy-3-(3-tetradecylphenoxy]-propoxy]phosphinyl]oxy]phenyl]methyl]-5-methyl-thiazolium, hydroxide, inner salt 3-[[3-[[hydroxy[2-ethoxy-3-(3-tetradecylphenoxy]-propoxy]phosphinyl]oxy]phenyl]methyl]-2-(2-methylpropyl)-thiazolium, hydroxide, inner salt 3-[[3-[[hydroxy[2-ethoxy-3-(2-pentadecylphenoxy]-propoxy]phosphinyl]oxy]phenyl]methyl]thiazolium, hydroxide, inner salt 3-[[3-[[hydroxy[2-ethoxy-3-(2-pentadecylphenoxy]-propoxy]phosphinyl]oxy]phenyl]methyl]-5-methyl-thiazolium, hydroxide, inner salt 3-[[3-[[hydroxy[2-ethoxy-3-(2-pentadecylphenoxy]-propoxy]phosphinyl]oxy]phenyl]methyl]-2-(2-methylpropyl)-thiazolium, hydroxide, inner salt 3-[[3-[[hydroxy[2-ethoxy-3-(4-tetradecylphenoxy]-propoxy]phosphinyl]oxy]phenyl]methyl]thiazolium, hydroxide, inner salt 3-[[3-[[hydroxy[2-ethoxy-3-(4-tetradecylphenoxy]-propoxy]phosphinyl]oxy]phenyl]methyl]-2-(2-methylpropyl)-thiazolium, hydroxide, inner salt 3-[[3-[[hydroxy[2-ethoxy-3-(3-dodecylphenoxy)propoxy]phosphinyl]oxy]phenyl]methyl]thiazolium, hydroxide, inner salt 3-[[3-[[hydroxy[2-ethoxy-3-(3-dodecylphenoxy)propoxy]phosphinyl]oxy]phenyl]methyl]-5-methyl-thiazolium, hydroxide, inner salt

EXAMPLE 21

3-[[3-[[[3-(Hexadecyloxy)-2-methoxypropoxy]hydroxyphosphinyl]oxy]phenyl]methyl]-5-methyl-thiazolium, hydroxide, inner salt To a solution of 7.42 g of 3-(hexadecyloxy)-2-methoxy-1-propanol in 90 ml of carbon tetrachloride cooled in an ice bath, was added with stirring 8.19 g of 3-(bromomethyl)phenyl phosphordichlorodate acid ester in 15 ml of carbon tetrachloride. A solution of 2.73 g of triethylamine in 15 ml of carbon tetrachloride was added dropwise. The mixture was stirred in the ice bath for 15 minutes, then at room temperature for 18 hours, filtered, washed with carbon tetrachloride and evaporated. The residue was stirred in a mixture of 190 ml of tetrahydrofuran and 190 ml of 0.5M sodium acetate for 2 hours, then the tetrahydrofuran was removed. The aqueous remainder was acidified with hydrochloric acid and extracted twice with ether. The extracts were combined, washed with brine, dried and evaporated. The residue was purified by chromatography, giving 7.9 g of 3-(bromomethyl)phenyl-3-(hexadecyloxy)phosphoric acid-2-methoxypropyl ester.

A mixture of 1.5 g of the above ester, 1.83 g of 5-methylthiazole and 15 ml of toluene was stirred at 60°–70° C. under argon for 24 hours, then allowed to stand at room temperature for 48 hours and evaporated. The residue was dissolved in 40 ml of methanol, stirred with 1.5 g of Amberlite ® IR-4B ion exchange resin for 2 hours, filtered and evaporated. The residue was purified by chromatography, then triturated with ether, giving 1.11 g of the desired product as a glass.

EXAMPLE 22

3-Hexadecyloxy-2-methoxypropylphosphoric acid, 3-(1H-imidazol-1-ylmethyl)phenyl ester A solution of 1.49 g of 3-(bromomethyl)phenyl, 3-(hexadecyloxy)-2-methoxypropyl ester and 1.4 g of imidazole in 10 ml of toluene was stirred at 65° C. under argon for 24 hours, then filtered from solid, the filtrate was evaporated. The residue was purified by chromatography giving 775 mg of the desired product as a glass.

EXAMPLE 23

1-[[3-[[[3-(Hexadecyloxy)-2-methoxypropoxy]hydroxyphosphinyl]oxy]phenyl]methyl]-3-methyl-1H-imidazolium, hydroxide, inner salt To a solution of 321 mg of 3-hexadecyloxy-2-methoxypropylphosphoric acid, 3-(1H-imidazol-1-ylmethyl)-phenyl ester in 5 ml of toluene was added 482 mg of methyl iodide. This mixture was heated at 65°–70° C. in a pressure bottle for 2 hours and then purified by chromatography, giving 300 mg of the desired product as a waxy solid.

EXAMPLE 24

3-[[2-[[[3-(Hexadecyloxy)-2-methoxypropoxy]hydroxyphosphinyl]oxy]phenyl]methyl]thiazolium, hydroxide, inner salt To a solution of 2.5 g of 3-(hexadecyloxy)-2-methoxy-1-propanol and 1.78 g of 2-chloro-4H-1,3,2-benzodioxaphosphorin, 2-oxide in 25 ml of carbon tetrachloride was added 995 mg of triethylamine. After stirring 5 hours the mixture was filtered and evaporated. The residue was dissolved in 40 ml of toluene and 10.3 g of thiazole was added. This mixture was maintained in a pressure bottle at 80° C. for 3 days then at room temperature for 2 days and evaporated. The residue was purified by chromatography.

EXAMPLE 25

3-[[3-[[[3-(Hexadecyloxy)-2-methoxypropoxy]hydroxyphosphinyl]oxy]phenyl]methyl]thiazolium, hydroxide, inner salt To a solution of 2 g of 3-(bromomethyl)phenyl phosphoric acid, 3-(hexadecyloxy)-2-methoxypropyl ester in 10 ml of toluene was added 2.3 g of thiazole. The mixture was stirred under argon at 65°–70° C. for 18 hours and then evaporated. The residue was dissolved in 50 ml of methanol and stirred with 500 mg of silver carbonate at room temperature for 2 hours, then filtered and evaporated. The residue was purified by chromatography giving 1.4 g of the desired product as an orange glass.

EXAMPLE 26

1-[[3-[[[3-(Hexadecyloxy)-2-methoxypropoxy]hydroxyphosphinyl]oxy]phenyl]methyl]pyridinium, hydroxide, inner salt To a solution of 2 g of 3-(bromomethyl)phenyl phosphoric acid, 3-(hexadecyloxy)-2-methoxypropyl ester in 10 ml of dry toluene was added 2.18 g of dry pyridine. The solution was stirred under argon at 60°–65° C. for 17 hours and then evaporated. The residue was dissolved in 50 ml of methanol, 2 g of methanol washed Amberlite ® IR-4B ion exchange resin was added, the mixture stirred 1 hour, filtered, washed with methanol and evaporated. The residue was purified by chromatography giving 1.9 g of the desired product as white powdered glass.

EXAMPLE 27

2-[[3-[[[3-(Hexadecyloxy)-2-methoxypropoxy]hydroxyphosphinyl]oxy]phenyl]methyl]isoquinolinium, hydroxide, inner salt To a solution of 2 g of 3-(bromomethyl)phenyl-3-(hexadecyloxy)phosphoric acid-2-methoxypropyl ester in 15 ml of hot toluene was added 3.56 g of isoquinoline. The solution was stirred at 60°-65° C. in an oil bath under argon overnight and then evaporated. The residue was dissolved in 50 ml of methanol and stirred with 2 g of methanol washed Amberlite ® IR-4B ion exchange resin for 1.5 hours, then filtered and evaporated to a syrup. The syrup was purified by chromatography then triturated with ether, giving 2 g of the desired product as a hard amorphous glass.

EXAMPLE 28

3-[[3-[[[3-(Hexadecyloxy)-2-methoxypropoxy]hydroxyphosphinyl]oxy]phenyl]methyl]-4,5-dimethythiazolium, hydroxide, inner salt A solution of 1.5 g of 3-(bromomethyl)phenyl-3-(hexadecyloxy)phosphoric acid-2-methoxypropyl ester and 2.34 g of 4,5-dimethylthiazole in 15 ml of dry toluene was stirred at 65° C. overnight, then at room temperature for 24 hours and evaporated. The residue was stirred with 1,5 g of methanol washed Amberlite ® IR-4B ion exchange resin in 40 ml of methanol for 2 hours, then filtered and evaporated. The residue was purified by chromatography, giving 1.1 g of the desired product as a wax.

EXAMPLE 29

3-[[3-[[[3-(Hexadecyloxy)-2-methoxypropoxy]hydroxyphosphinyl]oxy]phenyl]methyl]-2-(2-methylpropyl)-thiazolium, hydroxide, inner salt A solution of 2.01 g of 3-(bromomethyl)phenyl-3-(hexadecyloxy)phosphoric acid-2-methoxypropyl ester and 3.47 g of 2-isobutylthiazole in 15 ml of toluene was stirred at 65° C. for 24 hours under argon and then evaporated. The residue was stirred with 2 g of methanol washed Amberlite ® IR-4B ion exchange resin in 50 ml of methanol for 2 hours, then filtered and evaporated. The residue was purified by chromatography giving 1.01 g of the desired product as a waxy solid.

EXAMPLE 30

3-[[3-[[[3-(Hexacyloxy)-2-[(2-methyl-2-propenyl)oxy]propoxy]hydroxyphosphinyl]oxy]phenyl]methyl]-thiazolium, hydroxide, inner salt A 5.6 g portion of 3-(hexadecyloxy)-2-[(2-methyl-2-propenyl) oxy]-1-propanol in 60 ml of carbon tetrachloride, cooled in an ice bath was added a solution of 6.43 g of 3-(bromomethyl)phenyl phosphorodichlorodate in 10 ml of carbon tetrachloride. To this was added dropwise, a solution of 2.18 g of triethylamine in 10 ml of carbon tetrachloride. The mixture was then stirred at room temperature for 18 hours, filtered and evaporated. The residue was hydrolyzed in a mixture of 145 ml of tetrahydrofuran and 145 ml of 0.5M sodium acetate for 2 hours, then the tetrahydrofuran was removed. The aqueous remainder was acidified with concentrated hydrochloric acid and extracted twice with ether. The extracts were combined, washed with brine, dried and evaporated. The residue was purified by chromatography giving 7 g of 3-(hexadecyloxy)-2-[(2-methyl-2-propenyl)oxy]propylphosphoric acid, 3-(bromomethyl)phenyl ester.

To a solution of 2 g of the above ester in 15 ml of toluene was added 2.2 g of thiazole. The solution was stirred at 65° C. for 24 hours, allowed to stand 48 hours at room temperature and then evaporated. The residue was stirred with 2 g of methanol washed Amberlite ® IR-4B ion exchange resin in 50 ml of methanol for 2 hours, then filtered and evaporated. The residue was purified by chromatography, then triturated with ether and refrigerated, giving 1.5 g of the desired product as a white amorphous solid.

EXAMPLE 31

3-[[2-[[[3-(Hexadecyloxy)-2-[(2-methyl-2-propenyl)oxy]propoxy]hydroxyphosphinyl]oxy]phenyl]methyl]-thiazolium, hydroxide, inner salt To a solution of 2.5 g of 3-(hexadecyloxy)-2-[(2-methyl-2-propenyl)oxy]-1-propanol and 1.59 g of 2-chloro-4H-1,3,2-benzodioxaphosphorin in 25 ml of carbon tetrachloride was added 853 mg of triethylamine. This mixture was stirred overnight and then evaporated. The residue was combined with 6.89 g of thiazole and 40 ml of toluene, heated at 90° C. for 3 days, then evaporated. The residue was stirred with 20 g of Amberlite ® IR-4B ion exchange resin in 100 ml of methanol for 10 minutes, then filtered and evaporated. The residue was purified by chromatography, giving the desired product.

EXAMPLE 32

N,N-Dimethylcarbamimidothioic acid, [3-[[[3-(hexadecyloxy)-2-methoxypropoxy]hydroxyphosphinyl]oxy]phenyl]methyl ester, monohydrobromide To a solution of 1.43 g of 3-(bromomethyl)phenyl-3-hexadecyloxyphosphoric acid, 2-methoxypropyl ester in 25 ml of absolute ethanol was added 259 mg of N,N-dimethylthiourea. The solution was stirred under argon at 75° C. overnight and then evaporated, giving the desired product as a white glass.

EXAMPLE 33

Carbamimidothioic acid, [3-[[[3-(hexdecyloxy)-2-methoxypropoxy]hydroxyphosphinyl]oxy]phenyl]methyl ester, monohydrobromide To a solution of 1.38 g of 3-(bromomethyl)phenyl-3-hexadecyloxyphosphoric acid, 2-methoxypropyl ester in 25 ml of absolute ethanol was added 181 mg of thiourea. The solution was stirred under argon at 75° C. for 18 hours and then evaporated, giving the desired product as a white glass.

EXAMPLE 34

3-(Hexadecyloxy)-2-methoxy-1-propanol, 4-methylbenzene sulfonate

A mixture of 9 g of 3-(hexadecyloxy)-2-methoxy-1-propanol, 5.09 g of tosyl chloride, 40 ml of pyridine and 40 ml of ether was allowed to stand for 3 days, then the ether was removed and the mixture refrigerated overnight. The mixture was then poured into water and extracted with ether. The ether extract was washed with dilute hydrochloric acid, dried and evaporated, giving 11.7 g of the desired compound as a yellow oil.

EXAMPLE 35

3-[[3-(Hexadecyloxy)-2-methoxypropoxy]methyl]benzenemethanol

To a suspension of 2.8 g of sodium hydride in 25 ml of dimethylformamide was added at 0° C. over 30 minutes a solution of 1,3-benzenedimethanol in 75 ml of dimethylformamide. After 30 minutes a solution of 3-(hexadecyloxy)-2-methoxy-1-propanol, 4-methyl benzene sulfonate in 25 ml of dimethylformamide was added over 30 minutes. After stirring 18 hours the mixture was poured into water and extracted with ethylacetate. The solution was dried and the product was purified by chromatography giving 4.7 g.

EXAMPLE 36

1-(Bromomethyl)-3-[[3-(hexadecyloxy)-2-methoxypropoxy]methyl]benzene

To a solution of 4 g of 3-[[3-(hexadecyloxy)-2-methoxypropoxy]methyl]benzenemethanol and 3.05 g of mesyl chloride in 40 ml of tetrahydrofuran at 0° C. was added over 20 minutes a solution of 2.69 g of triethylamine in 10 ml of tetrahydrofuran. A 7.71 g portion of lithium bromide was added and the mixture was stirred at room temperature for 2 hours. The solution was diluted with ether, poured into water, and extracted with ethanol. The extract was washed with saturated sodium bicarbonate solution, dried and evaporated, giving the desired compound as an oil.

According to the methods described in detail hereinabove in Examples 21-36, the compounds of this invention listed hereinbelow in Table VII can be prepared using the appropriate nitrogen containing heterocycle, phosphorous reagent and alcohol. The alcohols are obtained as described in detail in the U.S. Pat. Nos. 4,640,913, 4,697,031, 4,703,130 and 4,699,990 and our copending applications, and the following reference: Terashita z., et al, Life Sci. 32, 1975 (1983). The compounds of this invention can be prepared as the individual optically active R and S enantiomers or as the racemic mixtures as described in the formentioned patents and applications.

3-[[3-[[[3-(hexadecyloxy)-2-propoxypropoxy]hydroxyphosphinyl]oxy]phenyl]methyl]thiazolium, hydroxide, inner salt 3-[[3-[[[3-(tetradecyloxy)-2-methoxypropoxy]hydroxyphosphinyl]oxy]phenyl]methyl]-5-methylthiazolium, hydroxide, inner salt 3-[[3-[[[3-(hexadecyloxy)-2-ethoxypropoxy]hydroxyphosphinyl]oxy]phenyl]methyl]thiazolium, hydroxide, inner salt 3-[[3-[[[3-(hexadecyloxy)-2-ethoxypropoxy]hydroxyphosphinyl]oxy]phenyl]methyl]-5-methylthiazolium, hydroxide, inner salt 3-[[3-[[[3-(octadecyloxy)-2-methoxypropoxy]hydroxyphosphinyl]oxy]phenyl]methyl]thiazolium, hydroxide, inner salt 3-[[3-[[[3-(octadecyloxy)-2-methoxypropoxy]hydroxyphosphinyl]oxy]phenyl]methyl]-5-methylthiazolium, hydroxide, inner salt 3-[[2-[[[3-(tetradecyloxy)-2-methoxypropoxy]hydroxyphosphinyl]oxy]phenyl]methyl]thiazolium, hydroxide, inner salt 3-[[2-[[[3-(hexadecyloxy)-2-methoxypropoxy]hydroxyphosphinyl]oxy]phenyl]methyl]-5-methylthiazolium, hydroxide, inner salt 3-[[2-[[[3-(hexadecyloxy)-2-ethoxypropoxy]hydroxyphosphinyl]oxy]phenyl]methyl]thiazolium, hydroxide, inner salt 3-[[2-[[[3-(hexadecyloxy)-2-ethoxypropoxy]hydroxyphosphinyl]oxy]phenyl]methyl]-5-methylthiazolium, hydroxide, inner salt 3-[[2-[[[3-(octadecyloxy)-2-methoxypropoxy]hydroxyphosphinyl]oxy]phenyl]methyl]thiazolium, hydroxide, inner salt 3-[[2-[[[3-(octadecyloxy)-2-ispropoxypropoxy]hydroxyphosphinyl]oxy]phenyl]methyl]-3,5-dimethylthiazolium, hydroxide, inner salt 3-[[4-[[[3-(hexadecyloxy)-2-methoxypropoxy]hydroxyphosphinyl]oxy]phenyl]methyl]thiazolium, hydroxide, inner salt 3-[[4-[[[3-(hexadecyloxy)-2-methoxypropoxy]hydroxyphosphinyl]oxy]phenyl]methyl]-5-methylthiazolium, hydroxide, inner salt 3-[[4-[[[3-(hexadecyloxy)-2-ethoxypropoxy]hydroxyphosphinyl]oxy]phenyl]methyl]thiazolium, hydroxide, inner salt 3-[[4-[[[3-(hexadecyloxy)-2-ethoxypropoxy]hydroxyphosphinyl]oxy]phenyl]methyl]-5-methylthiazolium, hydroxide, inner salt 3-[[4-[[[3-(octadecyloxy)-2-methoxypropoxy]hydroxyphosphinyl]oxy]phenyl]methyl]thiazolium, hydroxide, inner salt 3-[[4-[[[3-(octadecyloxy)-2-methoxypropoxy]hydroxyphosphinyl]oxy]phenyl]methyl]-5-methylthiazolium, hydroxide, inner salt 1-[[3-[[[3-(hexadecyloxy)-2-methoxypropoxy]hydroxyphosphinyl]oxy]phenyl]methyl]-3-methylpyridinium, hydroxide, inner salt 1-[[3-[[[3-(hexadecyloxy)-2-methoxypropoxy]hydroxyphosphinyl]oxy]phenyl]methyl]-3-ethyl-1H-imidazolium, hydroxide, inner salt 1-[[3-[[[3-(hexadecyloxy)-2-ethoxypropoxy]hydroxyphosphinyl]oxy]phenyl]methyl]-3-methyl-1H-imidazolium, hydroxide, inner salt 1-[[3-[[[3-(hexadecyloxy)-2-ethoxypropoxy]hydroxyphosphinyl]oxy]phenyl]methyl]pyridinium, hydroxide, inner salt 1-[[3-[[[3-(hexadecyloxy)-2-ethoxypropoxy]hydroxyphosphinyl]oxy]phenyl]methyl]-3-ethyl-1H-imidazolium, hydroxide, inner salt 1-[[3-[[[3-(hexadecyloxy)-2-propoxypropoxy]hydroxyphosphinyl]oxy]phenyl]methyl]-3-methyl-1H-imidazolium, hydroxide, inner salt 1-[[2-[[[3-(hexadecyloxy)-2-methoxypropoxy]hydroxyphosphinyl]oxy]phenyl]methyl]quinolinium, hydroxide, inner salt 1-[[2-[[[3-(hexadecyloxy)-2-methoxypropoxy]hydroxyphosphinyl]oxy]phenyl]methyl]-3-propyl-1H-imidazolium, hydroxide, inner salt 1-[[2-[[[3-(hexadecylpoxy)-2-methoxypropoxy]hydroxyphosphinyl]oxy]phenyl]methyl]-3-methyl-1H-imidazolium, hydroxide, inner salt 1-[[2-[[[3-(hexadecyloxy)-2-isobutoxypropoxy]hydroxyphosphinyl]oxy]phenyl]methyl]quinolinium, hydroxide, inner salt 1-[[2-[[[3-(hexadecyloxy)-2-ethoxypropoxy]hydroxyphosphinyl]oxy]phenyl]methyl]-3-ethyl-1H-imidazolium, hydroxide, inner salt
1-[[2-[[[3-(hexadecyloxy)-2-ethoxypropoxy]hydroxyphosphinyl]oxy]phenyl]methyl]-3-methyl-1H-imidazolium, hydroxide, inner salt
1-[[2-[[[3-(octadecyloxy)-2-methoxypropoxy]hydroxyphosphinyl]oxy]phenyl]methyl]quinolinium, hydroxide, inner salt
1-[[4-[[[3-(hexadecyloxy)-2-methoxypropoxy]hydroxyphosphinyl]oxy]phenyl]methyl]pyridinium, hydroxide, inner salt
1-[[4-[[[3-(hexadecyloxy)-2-methoxypropoxy]hydroxyphosphinyl]oxy]phenyl]methyl]quinolinium, hydroxide, inner salt
1-[[4-[[[3-(hexadecyloxy)-2-methoxypropoxy]hydroxyphosphinyl]oxy]phenyl]methyl]-3-propyl-1H-imidazolium, hydroxide, inner salt
1-[[4-[[[3-(hexadecyloxy)-2-methoxypropoxy]hydroxyphosphinyl]oxy]phenyl]methyl]-3-methyl-1H-imidazolium, hydroxide, inner salt
1-[[4-[[[3-(hexadecyloxy)-2-ethoxypropoxy]hydroxyphosphinyl]oxy]phenyl]methyl]pyridinium, hydroxide, inner salt
1-[[-4-[[[3-(hexadecyloxy)-2-ethoxypropoxy]hydroxyphosphinyl]oxy]phenyl]methyl]quinolinium, hydroxide, inner salt
1-[[4-[[[3-(hexadecyloxy)-2-ethoxypropoxy]hydroxyphosphinyl]oxy]phenyl]methyl]-3-ethyl-1H-imidazolium, hydroxide, inner salt
1-[[4-[[[3-(hexadecyloxy)-2-ethoxypropoxy]hydroxyphosphinyl]oxy]phenyl]methyl]-3-methyl-1H-imidazolium, hydroxide, inner salt
1-[[4-[[[3-(octadecyloxy)-2-methoxypropoxy]hydroxyphosphinyl]oxy]phenyl]methyl]quinolinium, hydroxide, inner salt
3-[[3-[[[3-(octadecyloxy)-2-methoxypropoxy]hydroxyphosphinyl]oxy]phenyl]methyl]isoquinolinium, hydroxide, inner salt
1-[[3-[[[3-(hexadecyloxy)-2-methoxypropoxy]hydroxyphosphinyl]oxy]phenyl]methyl]pyridazinium, hydroxide, inner salt
1-[[3-[[[3-(hexadecyloxy)-2-methoxypropoxy]hydroxyphosphinyl]oxy]phenyl]methyl]pyrimidinium, hydroxide, inner salt
1-[[3-[[[3-(hexadecyloxy)-2-methoxypropoxy]hydroxyphosphinyl]oxy]phenyl]methyl]pyrazinium, hydroxide, inner salt

EXAMPLE 37

3-[[3-[[3-(Hexadecyloxy)-2-methoxypropoxy]methyl]phenyl]methyl]thiazolium bromide To a solution of 4 g of 3-[[3-(hexadecyloxy)-2-methoxypropoxy]methyl]benzenemethanol and 3.05 g of mesyl chloride in 40 ml of tetrahydrofuran at 0° C. was added over 20 minutes a solution of 2.69 g of triethylamine in 10 ml of tetrahydrofuran. A 7.71 g portion of lithium bromide was added and the mixture was stirred for 2 hours, diluted with water and filtered. The filtrate was poured into water and extracted with ether. The ether extract was washed with saturated sodium bicarbonate, dried and evaporated, giving 4.5 g of 1-(bromomethyl)-3-[[3-(hexadecyloxy)-2-methoxypropoxy]methyl]benzene as an oil.

A mixture of 2.5 g of the above oil, 4.14 g of thiazole and 40 ml of toluene was stirred and heated at 70°-75° C., under argon in a pressure bottle for 48 hours and then evaporated. The residue was purified by chromatography and crystallized from ether, giving 2.2 g of the desired product as a white powder.

EXAMPLE 38

1-[[3-[[3-(Hexadecyloxy)-2-methoxypropoxy]methyl]phenyl]methyl]-1H-imidazole

A mixture of 2.4 g of 1-(bromomethyl)-3-[[3-(hexadecyloxy)-2-methoxypropoxy]methyl]benzene, 2.54 g of imidazole and 30 ml of toluene was heated at 80° C. under argon in a pressure bottle for 4 hours and then evaporated. The residue was purified by chromatography, giving 2.02 g of the desired product as a colorless oil.

EXAMPLE 39

1-[[3-[[3-(Hexadecyloxy)-2-methoxypropoxy]methyl]phenyl]methyl]-3-methyl-1H-imidazolium, iodide A mixture of 1.4 g of 1-[[3-[[3-(hexadecyloxy)-2-methoxypropoxy]methyl]phenyl]methyl]-1H-imidazole, 2.38 g of methyl iodide and 15 ml of toluene was heated at 80° C. for 2 hours and then evaporated. The residue was purified by chromatography and then crystallized from ether, giving 1.6 g of the desired product as a light yellow powder.

EXAMPLE 40

3-[[3-[[3-(Hexadecyloxy)-2-methoxypropoxy]carbonyl]phenyl]methyl]thiazolium, bromide A solution of 12 g of m-bromomethylbenzoic acid 10.62 g of oxalyl chloride, 100 ml of dichloromethane and 5 drops of dimethylformamide was allowed to stand 48 hours and then evaporated. Hexane and ether were added, the mixture evaporated and the residue distilled on a Kugelroher, giving 12.5 g of m-bromomethylbenzoyl chloride as a yellow liquid.

A mixture of 8 g of 3-(hexadecyloxy)-2-methoxypropanol, 6.22 g of m-bromomethylbenzoyl chloride, 2.11 g of pyridine and 80 ml of tetrahydrofuran was stirred for 48 hours, then filtered and evaporated. The residue was purified by chromatography and crystallized giving 10 g of 3-(bromomethyl)benzoic acid, 3-(hexadecyloxy)-2-methoxypropyl ester as white solid.

A mixture of 2 g of the above ester, 5.16 g of thiazole and 15 ml of toluene was stirred at 65° C. under argon for 3 days, then at reflux for 4 days and evaporated. The residue was purified by chromatography, giving 440 mg of the desired product as a yellow foam.

According to the methods described in detail hereinabove in Examples 37-39, the compounds of this invention listed hereinbelow in Table VIII can be prepared using the appropiate nitrogen containing heterocyle, phosphorous reagent and alcohol. The alcohols are obtained as described in detail in the U.S. Pat. No. 4,640,913, our copending applications, and the following reference: Terashita z., et al, Life Sci. 32, 1975 (1983). The compounds of this invention can be prepared as the individual optically active R and S enantiomers or as the racemic mixtures as described in the formentioned patent and applications.

TABLE VIII

3-[[3-[[3-(hexadecyloxy)-2-propoxypropoxy]methyl]phenyl]methyl]thiazolium, Bromide
3-[[3-[[3-(tetradecyloxy)-2-methoxypropoxy]methyl]phenyl]methyl]-5-methylthiazolium, Bromide 3-[[3-[[3-(hexadecyloxy)-2-ethoxypropoxy]methyl]-
phenyl]methyl]thiazolium, Bromide
3-[[3-[[3-(hexadecyloxy)-2-ethoxypropoxy]methyl]-
phenyl]methyl]-5-methylthiazolium, Bromide
3-[[3-[[3-(octadecyloxy)-2-methoxypropoxy]methyl]-
phenyl]methyl]thiazolium, Bromide
3-[[3-[[3-(octadecyloxy)-2-methoxypropoxy]methyl]-
phenyl]methyl]-5-methylthiazolium, Bromide
3-[[2-[[3-(tetradecyloxy)-2-methoxypropoxy]methyl]-
phenyl]methyl]thiazolium, Bromide
3-[[2-[[3-(hexadecyloxy)-2-methoxypropoxy]methyl]-
phenyl]methyl]-5-methylthiazolium, Bromide
3-[[2-[[3-(hexadecyloxy)-2-ethoxypropoxy]methyl]-
phenyl]methyl]thiazolium, Bromide
3-[[2-[[3-(hexadecyloxy)-2-ethoxypropoxy]methyl]-
phenyl]methyl]-5-methylthiazolium, Bromide
3-[[2-[[3-(octadecyloxy)-2-methoxypropoxy]methyl]-
phenyl]methyl]thiazolium, Bromide
3-[[2-[[3-(octadecyloxy)-2-ispropoxypropoxy]methyl]-
phenyl]methyl]-3,5-dimethylthiaozlium, Bromide
3-[[4-[[3-(hexadecyloxy)-2-methoxypropoxy]methyl]-
phenyl]methyl]thiazolium, Bromide
3-[[4-[[3-(hexadecyloxy)-2-methoxypropoxy]methyl]-
phenyl]methyl]-5-methylthiazolium, Bromide
3-[[4-[[3-(hexadecyloxy)-2-ethoxypropoxy]methyl]-
phenyl]methyl]thiazolium, Bromide
3-[[4-[[3-(hexadecyloxy)-2-ethoxypropoxy]methyl]-
phenyl]methyl]-5-methylthiazolium, Bromide
3-[[4-[[3-(octadecyloxy)-2-methoxypropoxy]methyl]-
phenyl]methyl]thiazolium, Bromide
3-[[4-[[3-(tetradecyloxy)-2-methoxypropoxy]methyl]-
phenyl]methyl]-5-methylthiazolium, Bromide
1-[[3-[[3-(hexadecyloxy)-2-methoxypropoxy]methyl]-
phenyl]methyl]-3-methylpyridinium, Bromide
1-[[3-[[3-(hexadecyloxy)-2-methoxypropoxy]methyl]-
phenyl]methyl]-3-ethyl-1H-imidazolium, Iodide
1-[[3-[[3-(hexadecyloxy)-2-ethoxypropoxy]methyl]-
phenyl]methyl]-3-methyl-1H-imidazolium, Iodide
1-[[3-[[3-(hexadecyloxy)-2-ethoxypropoxy]methyl]-
phenyl]methyl]pyridinium, Bromide
1-[[3-[[3-(hexadecyloxy)-2-ethoxypropoxy]methyl]-
phenyl]methyl]-3-ethyl-1H-imidazolium, Bromide
1-[[3-[[3-(hexadecyloxy)-2-propoxypropoxy]methyl]-
phenyl]methyl]-3-methyl-1H-imidazolium, Bromide
1-[[2-[[3-(hexadecyloxy)-2-methoxypropoxy]methyl]-
phenyl]methyl]quinolinium, Bromide
1-[[2-[[3-(hexadecyloxy)-2-methoxyporpoxy]methyl]-
phenyl]methyl]-3-propyl-1H-imidazolium, Bromide
1-[[2-[[3-(hexadecyloxy)-2-methoxypropoxy]methyl]-
phenyl]methyl]-3-methyl-1H-imidazolium, Bromide
1-[[2-[[3-(hexadecyloxy)-2-isobutoxypropoxy]methyl]-
phenyl]methyl]quinolinium, Bromide
1-[[2-[[3-(hexadecyloxy)-2-ethoxypropoxy]methyl]-
phenyl]methyl]-3-ethyl-1H-imidazolium, Bromide
1-[[2-[[3-(hexadecyloxy)-2-ethoxypropoxy]methyl]-
phenyl]methyl]-3-methyl-1H-imidazolium, Bromide
1-[[2-[[3-(octadecyloxy)-2-methoxypropoxy]methyl]-
phenyl]methyl]quinolinium, Bromide
1-[[4-[[3-(hexadecyloxy)-2-methoxypropoxy]methyl]-
phenyl]methyl]pyridinium, Bromide
1-[[4-[[3-(hexadecyloxy)-2-methoxypropoxy]methyl]-
phenyl]methyl]quinolinium, Bromide
1-[[4-[[3-(hexadecyloxy)-2-methoxypropoxy]methyl]-
phenyl]methyl]-3-propyl-1H-imidazolium, Bromide
1-[[4-[[3-(hexadecyloxy)-2-methoxypropoxy]methyl]-
phenyl]methyl]-3-methyl-1H-imidazolium, Bromide
1-[[4-[[3-(hexadecycloxy)-2-ethoxypropoxy]methyl]-
phenyl]methyl]pyridinium, Bromide
1-[[4-[[3-(hexadecyloxy)-2-ethoxypropoxy]methyl]-
phenyl]methyl]quinolinium, Bromide
1-[[4-[[3-(hexadecyloxy)-2-ethoxypropoxy]methyl]-
phenyl]methyl]-3-ethyl-1H-imidazolium, Bromide
1-[[4-[[3-(hexadecyloxy)-2-ethoxypropoxy]methyl]-
phenyl]methyl]-3-methyl-1H-imidazolium, Bromide
1-[[4-[[3-(octadecyloxy)-2-methoxypropoxy]methyl]-
phenyl]methyl]quinolinium, Bromide
3-[[3-[[3-(octadecyloxy)-2-methoxypropoxy]methyl]-
phenyl]methyl]isoquinolinium, Bromide
1-[[3-[[3-(hexadecyloxy)-2-methoxypropoxy]methyl]-
phenyl]methyl]pyridazinium, Bromide
1-[[3-[[3-(hexadecyloxy)-2-methoxypropoxy]methyl]-
phenyl]methyl]pyrimidinium, Bromide
1-[[3-[[3-(hexadecyloxy)-2-methoxypropoxy]methyl]-
phenyl]methyl]pyrazinium, Bromide

EXAMPLE 41

1-[[3-[[3-(Hexadecyloxy)-2-methoxypropoxy]car-
bonyl]phenyl]methyl]pyridazinium, bromide A mixture of 1.2 g of 3-(bromomethyl)benzoic acid, 3-(hexadecyloxy)-2-methoxypropyl ester, 1.46 g of pyridazine and 10 ml of toluene was heated in a pressure bottle at 100° C. for 1.5 hours, then evaporated. The residue was purified by chromatography, giving 150 mg of the desired product as a foam.

EXAMPLE 42

8-(Hexadecyloxy)-7-methoxy-1-octene

A mixture of 45 g of 7,8-dihydroxy-1-octene and 101.2 g of p-anisylchlorodiphenylmethane in 200 ml of pyridine was allowed to stand at 10° C. for 48 hours. The mixture was poured into water and extracted with ether. The ether solution was dried and evaporated. The residue was dissolved in 300 ml of dimethylformamide containing 83.1 ml of methyl iodide and this solution was added dropwise to a suspension of 17.75 g of 60% sodium hydride in 500 ml of dimethylformamide over a 2 hour period. After stirring an additional 13 hours the mixture was poured into water and extracted with ether. The ether solution was dried and evaporated. The residue was dissolved in 400 ml of methanol and stirred with 35 g of Amberlyst 15 resin. The solution was filtered and solvent was removed. The residue was purified by chromatography giving 22.6 g of 8-hydroxy-7-methoxy-1-octene as an oil.

To a suspension of 7.4 g of 60% sodium hydride in 100 ml of dimethylformamide was added a solution of 8-hydroxy-7-methoxy-1-octene in 150 ml of dimethylformamide over 1.5 hours. A 63.4 g portion of the tosylate of 1-hexadecanol was added and the mixture was stirred for 18 hours, poured into water and extracted with ether. The ether solution was dried and evaporated. The residue was purified by chromatography giving 41.5 g of the title compound as a oil.

According to the methods described in detail hereinabove in Examples 40 and 41, the compounds of this invention listed hereinbelow in Table IX can be prepared using the appropiate nitrogen containing heterocycle, phosphorous reagent and alcohol. The alcohols are obtained as described in detail in the U.S. Pat. Nos. 4,640,913, 4,697,031, 4,703,130 and 4,699,990 and our copending applications, and the following reference: Terashita Z., et al, Life Sci. 32, 1975 (1983). The compounds of this invention can be prepared as the individual optically active R and S enantiomers or as the racemic mixtures as described in the formentioned patents and applications.

TABLE IX

3-[[3-[[3-(hexadecyloxy)-2-propoxypropoxy]carbonyl]phenyl]methyl]thiazolium, Bromide 3-[[3-[(tetradecyloxy)-2-methoxypropoxy]carbonyl]phenyl]methyl]-5-methylthiazolium, Bromide 3-[[3-[[3-(hexadecyloxy)-2-ethoxypropoxy]carbonyl]phenyl]methyl]thiazolium, Bromide 3-[[3-[[3-(hexadecyloxy)-2-ethoxypropoxy]carbonyl]phenyl]methyl]-5-methylthiazolium, Bromide 3-[[3-[[3-(octadecyloxy)-2-methoxypropoxy]carbonyl]phenyl]methyl]thiazolium, Bromide 3-[[3-[[3-(octadecyloxy)-2-methoxypropoxy]carbonyl]phenyl]methyl]-5-methylthiazolium, Bromide 3-[[2-[[3-(tetradecyloxy)-2-methoxypropoxy]carbonyl]phenyl]methyl]thiazolium, Bromide 3-[[2-[[3-(hexadecyloxy)-2-methoxypropoxy]carbonyl]phenyl]methyl]-5-methylthiazolium, Bromide 3-[[2-[[3-(hexadecyloxy)-2-ethoxypropoxy]carbonyl]phenyl]methyl]thiazolium, Bromide 3-[[2-[[3-(hexadecyloxy)-2-ethoxypropoxy]carbonyl]phenyl]methyl]-5-methylthiazolium, Bromide 3-[[2-[[3-(octadecyloxy)-2-methoxypropoxy]carbonyl]phenyl]methyl]thiazolium, Bromide 3-[[2-[[3-(octadecyloxy)-2-isopropoxypropoxy]carbonyl]phenyl]methyl]-3,5-dimethylthiazolium, Bromide 3-[[4-[[3-(hexadecyloxy)-2-methoxypropoxy]carbonyl]phenyl]methyl]thiazolium, Bromide 3-[[4-[[3-(hexadecyloxy)-2-methoxypropoxy]carbonyl]phenyl]methyl]-5-methylthiazolium, Bromide 3-[[4-[[3-(hexadecyloxy)-2-ethoxypropoxy]carbonyl]phenyl]methyl]thiazolium, Bromide 3-[[4-[[3-(hexadecyloxy)-2-ethoxypropoxy]carbonyl]phenyl]methyl]-5-methylthiazolium, Bromide 3-[[4-[[3-(octadecyloxy)-2-methoxypropoxy]carbonyl]phenyl]methyl]thiazolium, Bromide 3-[[4-[[3-(tetradecyloxy)-2-methoxypropoxy]carbonyl]phenyl]methyl]-5-methylthiazolium, Bromide 1-[[3-[[3-(hexadecyloxy)-2-methoxypropoxy]carbonyl]phenyl]methyl]-3-methylpyridinium, Bromide 1-[[3-[[3-(hexadecyloxy)-2-methoxypropoxy]carbonyl]phenyl]methyl]-3-ethyl-1H-imidazolium, Iodide 1-[[3-[[3-(hexadecyloxy)-2-ethoxypropoxy]carbonyl]phenyl]methyl]-3-methyl-1H-imidazolium, Iodide 1-[[3-[[3-(hexadecyloxy)-2-ethoxypropoxy]carbonyl]phenyl]methyl]pyridinium, Bromide 1-[[3-[[3-(hexadecyloxy)-2-ethoxypropoxy]carbonyl]phenyl]methyl]-3-ethyl-1H-imidazolium, Bromide 1-[[3-[[3-(hexadecyloxy)-2-propoxypropoxy]carbonyl]phenyl]methyl]-3-methyl-1H-imidazolium, Bromide 1-[[2-[[3-(hexadecyloxy)-2-methoxypropoxy]carbonyl]phenyl]methyl]quinolinium, Bromide 1-[[2-[[3-(hexadecyloxy)-2-methoxypropoxy]carbonyl]phenyl]methyl]-3-propyl-1H-imidazolium, Bromide 1-[[4-[[3-(hexadecyloxy)-2-methoxypropoxy]carbonyl]phenyl]methyl]quinolinium, Bromide 1-[[4-[[3-(hexadecyloxy)-2-methoxypropoxy]carbonyl]phenyl]methyl]-3-propyl-1H-imidazolium, Chloride 1-[[4-[[3-(hexadecyloxy)-2-methoxypropoxy]carbonyl]phenyl]methyl]-3-methyl-1H-imidazolium, Bromide 1-[[4-[[3-(hexadecyloxy)-2-ethoxypropoxy]carbonyl]phenyl]methyl]pyridinium, Bromide 1-[[4-[[3-(hexadecyloxy)-2-ethoxypropoxy]carbonyl]phenyl]methyl]quinolinium, Bromide 1-[[2-[[3-(hexadecyloxy)-2-methoxypropoxy]carbonyl]phenyl]methyl]-3-methyl-1H-imidazolium, Bromide 1-[[2-[[3-(hexadecyloxy)-2-isobutoxypropoxy]carbonyl]phenyl]methyl]quinolinium, Bromide 1-[[2-[[3-(hexadecyloxy)-2-ethoxypropoxy]carbonyl]phenyl]methyl]-3-ethyl-1H-imidazolium, Bromide 1-[[2-[[3-(hexadecyloxy)-2-ethoxypropoxy]carbonyl]phenyl]methyl]-3-methyl-1H-imidazolium, Bromide 1-[[2-[[3-(octadecyloxy)-2-methoxypropoxy]carbonyl]phenyl]methyl]quinolinium, Bromide 1-[[4-[[3-(hexadecyloxy)-2-methoxypropoxy]carbonyl]phenyl]methyl]pyridinium, Bromide 1-[[4-[[3-(hexadecyloxy)-2-ethoxypropoxy]carbonyl]phenyl]methyl]-3-ethyl-1H-imidazolium, Bromide 1-[[4-[[3-(hexadecyloxy)-2-ethoxypropoxy]carbonyl]phenyl]methyl]-3-methyl-1H-imidazolium, Bromide 1-[[4-[[3-(octadecyloxy)-2-methoxypropoxy]carbonyl]phenyl]methyl]quinolinium, Bromide 3-[[3-[[3-(octadecyloxy)-2-methoxypropoxy]carbonyl]phenyl]methyl]isoquinolinium, Bromide 1-[[3-[[3-(hexadecyloxy)-2-methoxypropoxy]carbonyl]phenyl]methyl]-2-methylpyridinium, Iodide 1-[[3-[[3-(hexadecyloxy)-2-methoxypropoxy]carbonyl]phenyl]methyl]pyrimidinium, Bromide 1-[[3-[[3-(hexadecyloxy)-2-methoxypropoxy]carbonyl]phenyl]methyl]pyrazinium, Bromide

EXAMPLE 43

8-(Hexadecyloxy)-7-methoxy-1-octanol

To a solution of 8-(hexadecyloxy)-7-methoxy-1-octene in 100 ml of tetrahydrofuran was added a solution of 112.3 ml of 1.0M borane in tetrahydrofuran at 0° C. over a 1 hour period. The mixture was stirred on addition 3 hours at 25° C. The solution was recooled to 0° C. and a solution of 187.3 ml of 3M sodium hydroxide was slowly added followed by 216 ml of 30% hydrogen peroxide. After 30 minutes, the mixture was poured into water and extracted with ether. The ether solution was dried and evaporated. The residue was purified by chromatography giving 20 g of the title compound as a solid.

EXAMPLE 44

3-[[3-[[[[8-(Hexadecyloxy)-7-methoxyoctyl]oxy]hydroxyphosphinyl]oxy]phenyl]methyl]-, hydroxide, inner salt To a solution of 2.0 g of 8-(hexadecyloxy)-7-methoxy-1-octanol in 30 ml of dry carbon tetrachloride was added dropwise a solution of 1.8 g of 3-(bromomethyl)phenyl phosphodichlorodate in 5 ml of carbon tetrachloride. This mixture was cooled in an ice bath and a solution of 0.6 g of triethylamine in 5 ml carbon tetrachloride was added dropwise. This mixture was stirred under argon at room temperature overnight and then filtered. The filtrate was evaporated and the residue hydrolyzed in a mixture of 60 ml of tetrahydrofuran and 60 ml of 0.5 ml sodium acetate for 2 hours. The tetrahydrofuran was removed, the aqueous phase acidified and extracted three times with ether. The extracts were combined, washed with saturated sodium chloride, dried and evaporated.

To a solution of the residue in 15 ml of dry toluene was added 2.4 g of thiazole. This solution was stirred overnight in an oil bath at 65°-70° C. under argon and then evaporated. The residue was dissolved in 50 ml of methanol and stirred with 2 g of methanol washed Amberlite® IR-4B ion exchange resin for 1 hour, then filtered, washed with methanol and the combined filtrate and wash evaporated. The residue was purified by chromatography, giving 1.66 g of the desired product as a buff colored glass.

EXAMPLE 45

[2-(Hexadecyloxy)-1-(hydroxymethyl)ethoxy]acetic acid

To a suspension of 13.1 g of 50% sodium hydride in 200 ml of toluene was add a solution of 12.6 g of chloroacetic acid in 50 ml of toluene over a 45 minute period. A solution of 65.5 g of 1-(hexadecyloxy)-3-[(4-methoxyphenyl)diphenylmethoxy]-2-propanol in 100 ml of toluene was added over 30 minutes. The mixture was refluxed for 65 hours, poured into water and acidified to pH 4. The mixture was extracted with ether. The ether solution was dried and evaporated. The residue was purified by chromatography giving 22.3 g of the title compound.

EXAMPLE 46

3-[[3-[[Hydroxy[2-(2-methoxy-2-oxoethoxy)-3-(hexadecyloxy)propoxy]phosphinyl]oxy]phenyl]methyl]-hydroxide, inner salt To a solution of 2.6 g of [2-(hexadecyloxy)-1-(hydroxymethyl)ethoxy]acetic acid in 40 ml of dry carbon tetrachloride was added dropwise, a solution of 2.5 g of 3-(bromomethyl)phenyl phosphodichlorodate in 7 ml of carbon tetrachloride. This mixture was cooled in an ice bath and a solution of 0.84 g of triethylamine in 7 ml of carbon tetrachloride was added dropwise. This mixture was stirred under argon at room temperature overnight and then filtered. The filtrate was evaporated and the residue hydrolyzed in a mixture of 25 ml of tetrahydrofuran and 85 ml of 0.5M sodium acetate for 2 hours. The tetrahydrofuran was removed, the aqueous phase acidified and extracted three times with ether. The extracts were combined, washed with saturated sodium chloride, dried and evaporated.

The residue was dissolved in 30 ml of dry toluene and to this was added 4.7 g of thiazole. This solution was stirred overnight in an oil bath at 65°-70° C. under argon and then evaporated. The residue was dissolved in 50 ml of methanol and stirred with 3.5 g of methanol washed Amberlite® IR-4B ion exchange resin for 1 hour, then filtered, washed with methanol and the combined filtrate and wash evaporated. The residue was purified by chromatography using methanol-water-chloroform giving 1.058 g of the desired product as a buff colored glass.

EXAMPLE 47

3-[[3-[[1-Hydroxy-4-methoxy-2,6,9,12-tetraoxa-1-phosphadocosyl]oxy]phenyl]methyl], hydroxide, inner salt, P-oxide To a solution of 6.7 g of 3-[2-[2-(decyloxy)ethoxy]ethoxy]-2-methoxy-1-propanol in 75 ml of dry carbon tetrachloride was added dropwise a solution of 7.3 g of 3-(bromomethyl)phenyl phosphodichlorodate in 15 ml of carbon tetrachloride. This mixture was cooled in an ice bath and a solution of 2.43 g of triethylamine in 15 ml of carbon tetrachloride was added dropwise. This mixture was stirred under argon at room temperature for 5 hours and then filtered. The filtrate was evaporated and the residue hydrolyzed in a mixture of 170 ml of tetrahydrofuran and 170 ml of 0.5M sodium acetate for 5 hours. The tetrahydrofuran was removed, the aqueous phase acidified and extracted three times with ether. The extracts were combined, washed with saturated sodium chloride, dried and evaporated giving 8 g of an oil.

To a solution of 1.3 g of the above oil in 10 ml of dry toluene was added 1.8 g of thiazole. This solution was stirred overnight in an oil bath at 65°-70° C. under argon and then evaporated. The residue was dissolved in 35 ml of methanol and stirred with 1.3 g of methanol washed Amberlite® IR-4B ion exchange resin for 1 hour, then filtered, washed with methanol and the combined filtrate and wash evaporated. The residue was purified by chromatography, giving 0.548 g of the desired product as a glass.

EXAMPLE 48

3-(Bromomethyl)phenyl 2-[3-(dodecyloxy)-2-methylphenoxy]-2-ethoxyethyl phosphate A solution of 6.5 g of 3-[3-(dodecyloxy)-2-methylphenoxy]-2-ethoxy-]-propanol in 25 ml of carbon tetrachloride was treated under argon with a solution of 5.51 g of 3-(bromomethyl)phenyl phosphodichlorodate in 10 ml of carbon tetrachloride and 2.53 ml of triethylamine in 10 ml of carbon tetrachloride. This mixture was stirred at room temperature for 3 hours, at 0° C. for 18 hours, and then evaporated. The residue was added to a mixture 200 ml of tetrahydrofuran and 200 ml of 0.5N sodium acetate and stirred for 2.5 hours. The tetrahydrofuran was removed, the aqueous remainder acidified with dilute hydrochloric acid and extracted three times with ether. the extracts were combined, washed with brine, dried over magnesium sulfate, and evaporated giving 10.7 g of the desired product as an oil.

EXAMPLE 49

3-[[3-[[[3-[3-(dodecyloxy)-2-methylphenoxy]-2-ethoxypropoxy]hydroxyphosphinyl]oxy]phenyl]methyl]-5-methyl-thiazolium, hydroxide, inner salt In a pressure bottle a mixture of 5.2 g of 3-(bromomethyl)phenyl 2-[3-dodecyloxy)-2-methylphenoxy]-2-ethoxyethyl phosphate from Example 48, 4.81 g of 5-methylthiazole and 40 ml of toluene was stirred under argon at 75° C. for 4 hours. The solvent was evaporated and the residue stirred with 10 g of Amberlite® IR45 ion exchange resin in 70 ml of methanol for 15 minutes. The mixture was filtered, evaporated and the residue purified by chromatography. The produce was precipitated from ether, giving 3.0 g of the desired product as a white powder.

We claim:

1. A compound of R enantiomer or racemic mixture of compounds of the formula;

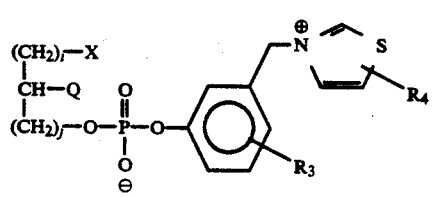

Formula I wherein:
(A) X is
(i) $C_1-C_{24}$ alkyl;
(ii) $C_1-C_{24}$ alkoxy;

(iii) $C_1$–$C_{24}$ carboamoyloxy;
(iiii)

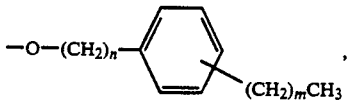

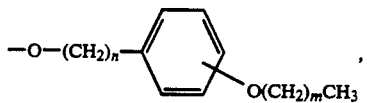

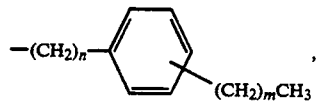

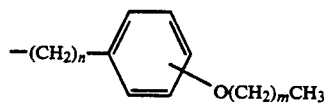

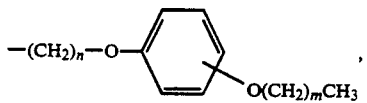

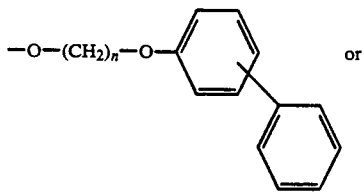 or

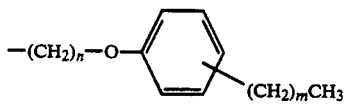

wherein n is an integer form 1 to 25 and m is an integer from 0 to 24 and the sum of n and m is less than or equal to 25;
(v) phenyl;
(vi) phenyl substituted with from 1 to 4 $C_1$–$C_{20}$ alkyl, $C_1$–$C_{20}$ alkoxy, halogen, trifluoromethyl, phenyl, or benzyloxy;
(vii) phenoxy;
(viii) phenoxy substituted with from 1 to 4 $C_1$–$C_{20}$ alkyl, $C_1$–$C_{20}$ alkoxy, halogen, trifluoromethyl, phenyl, or benzyloxy;
(ix) naphthaloxy;
(x) naphthaloxy substituted with from 1 to 4 $C_1$–$C_{20}$ alkyl, $C_1$–$C_{20}$ alkoxy or halogen; or
(xi) —O—$(CH_2)_r$—O—$((CH_2)_pO)_t$—$(CH_2)_a$—W wherein W is methyl or phenyl optionally substituted with $C_1$–$C_3$ alkyl, $C_1$–$C_3$ alkoxy or phenyl, r, p, t and a are integers such that the expression r+(p+1)t+a is also an integer and has a value of 3 to 20; r is greater than or equal to 2; p is greater than or equal to 2; t is greater than or equal to zero; and a is greater than or equal to zero;
(B) i is an integer from 1 to 3 and j is an integer from 1 to 6; and
(C) Q is —$OR_2$,

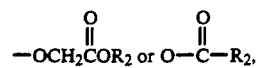

wherein $R_2$ is hydrogen, $C_1$–$C_6$ alkyl or $C_1$–$C_6$ alkenyl;
(D) the moiety $R_3$ represents one or more $C_1$–$C_5$ alkyl, $C_1$–$C_5$ alkoxy or halogen substituents of the aromatic ring; and
(E) the moiety $R_4$ represents one or more substituents of the heterocyclic ring which may occupy any non-hetero atom position and is
(i) $C_1$–$C_5$ alkyl;
(ii) $C_1$–$C_5$ alkoxy;
(iii) halogen;
(iv) —$CH_2CH_2OH$; or
(v) hydrogen 2. A compound according to claim 1 wherein X is
(i) $C_1$–$C_{24}$ alkoxy;
(ii)

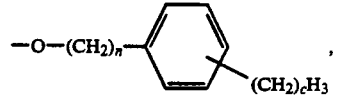

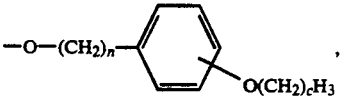

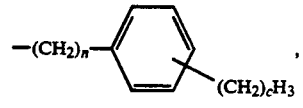

or

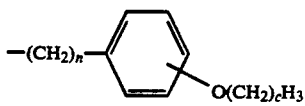

(iii) phenyl substituted with from 1 to 4 $C_1$–$C_{20}$ alkyl, $C_1$–$C_{20}$ alkoxy, halogen, trifluoromethyl, phenyl, substituted phenyl or benzyloxy; or phenoxy substituted with from 1 to 4 $C_1$–$C_{20}$ alkyl, $C_1$–$C_{20}$ alkoxy, halogen, trifluoromethyl, phenyl, substituted phenyl or benzyloxy.

3. The compound according to claim 1, 3-[[3-[[hydroxy-2-methoxy-3-[4-(phenylmethoxy)phenoxy]-propoxy]phosphinyl]oxy]phenyl]methyl]thiazolium, hydroxide, inner salt.

4. The compound according to claim 2, [[3-[[3-[[hydroxy[2-methoxy-3-(3-tetradecylphenoxy)propoxy]-phosphinyl]oxy]phenyl]methyl]thiazolium, hydroxide inner salt.

5. The compound according to claim 2, 3-[[3-[[[3-[3-(dodecyloxy)-2-methylphenoxy]-2-methoxypropoxy]-hydroxyphosphinyl]oxy]phenyl]methyl]-5-methyl-thiazolium, hydroxide, inner salt.

6. The compound according to claim 2, 3-[[3-[[[3-[3-(dodecyloxy)-2-methylphenoxy]-2-methoxypropoxy]-hydroxyphosphinyl]oxy]phenyl]methyl]thiazolium, hydroxide, inner salt.

7. The compound according to claim 2, 3-[[2-[[[3-3-(dodecyloxy)-2-methylphenoxy]-2-methoxypropoxy]- hydroxyphosphinyl]oxy]phenyl]methyl]thiazolium, hydroxide, inner salt.

8. The compound according to claim 1, 3-[[3-[[[3-[[4-[(4-chlorophenyl)methoxy]phenyl]methoxy]-2-methoxypropoxy]-hydroxyphosphinyl]oxy]phenyl]methyl]-thiazolium, hydroxide, inner salt.

9. The compound according to claim 2, 3-[[3-[[[3-[3-(dodecyloxy)-2-methylphenoxy]-2-methoxypropoxy]-hydroxyphosphinyl]oxy]phenyl]methyl]-5-(2-hydroxyethyl)-4-methylthiazolium, hydroxide, inner salt.

10. The compound according to claim 1, 3-[[3-[[[3-[[4-(dodecyloxy)-1-naphthalenyl]oxy]-2-methoxypropoxy]hydroxyphosphinyl]oxy]phenyl]methyl]-thiazolium, hydroxide, inner salt.

11. The compound according to claim 2, 3-[[3-[[hydroxy[2-methoxy-3-(4-tetradecylphenoxy)propoxy]-phosphinyl]oxy]phenyl]methyl]thiazolium, hydroxide, inner salt.

12. The compound according to claim 1, 3-[[3-[[[3-[[8-([1,1'-biphenyl]-4-yloxy)octyl]oxy]-2-methyoxypropoxy]-hydroxyphosphinyl]oxy]phenyl]methyl]-thiazolium, hydroxide, inner salt.

13. The compound according to claim 2, 3-[[3-[[[3-(hexadecyloxy)-2-methoxypropoxy]hydroxyphosphinyl]oxy]phenyl]methyl]-5-methyl-thiazolium, hydroxide, inner salt.

14. The compound according to claim 2, 3-[[2-[[[3-(hexadecyloxy)-2-methoxypropoxy]]hydroxyphosphinyl]oxy]phenyl]methyl]thiazolium, hydroxide, inner salt.

15. The compound according to claim 2, 3-[[3-[[[3-(hexadecyloxy)-2-methoxypropoxy]hydroxyphosphinyl]oxy]phenyl]methyl]thiazolium, hydroxide, inner salt.

16. The compound according to claim 2, 3-[[3-[[[3-(hexadecyloxy)-2-methoxypropy]hydroxyphosphinyl]oxy]phenyl]methyl]-4,5-dimethythiazolium, hydroxide, inner salt.

17. The compound according to claim 2, 3-[[3-[[[3-(hexadecyloxy)-2-methoxypropoxy]hydroxyphosphinyl]oxy]phenyl]methyl]-2-(2-methylpropyl)-thiazolium, hydroxide, inner salt.

18. The compound according to claim 2, 3-[[3-[[[3-(hexadecyloxy)-2-[(2-methyl-2-propenyl)oxy]propoxy]-hydroxyphosphinyl]oxy]phenyl]methyl]thiazolium, hydroxide, inner salt.

19. The compound according to claim 2, 3-[[2-[[[3-(hexadecyloxy)-2-[(2-methyl-2-propenyl)oxy]propoxy]-hydroxyphosphinyl]oxy]phenyl]methyl]thiazolium, hydroxide, inner salt.

20. The compound according to claim 2, 3-[[3-[[[3-[3-(dodecyloxy)-2-methylphenoxy]-2-ethoxypropoxy]-hydroxyphosphinyl]oxy]phenyl]methyl]-5-methyl-thiazolium, hydroxide, inner salt.

21. A method for inhibiting the biological effects of PAF in the upper respiratory track of a mammal which comprises administering to the mammal a compound of claim 1 in an amount to inhibit PAF effects.

22. A method of treating asthma in a mammal which comprises administering to the mammal an antiasthmatic amount of a compound of claim 1.

23. A method for treating anaphylactic and septic shock in a mammal which comprises administering to said mammal an effective amount of a compound of claim 1.

24. A method of treating adult respiratory distress syndrome in a mammal which comprises administering to the mammal an effective amount of a compound of claim 1.

25. A composition of matter in dosage unit form which comprises a compound of claim 1 in association with a pharmaceutically acceptable carrier.

26. A method for inhibiting the biological effects of PAF in the upper respiratory track of a mammal according to claim 21 wherein the compound is 3-[[3-[[[3-[3-(dodecyloxy)-2-methylphenoxy]-2-ethoxypropoxy]-hydroxyphosphinyl]oxy]phenyl]-methyl]-5-methyl-thiazolium, hydroxide, inner salt.

27. The compound according to claim 2, 3-[[2-[(1-hydroxy-4-methoxy-7-oxo-2,6-dioxa-8-aza-1-phosphahexacosyl)oxy]phenyl]methyl]thiazolium, hydroxide, inner salt, P-oxide.

28. The compound according to claim 2, 3-[[3-[(1-hydroxy-4-methoxy-7-oxo-2,6-dioxa-8-aza-1-phosphahexacosyl)oxy]phenyl]methyl]thiazolium, hydroxide, inner salt, P-oxide.

* * * * *